US010376357B2

(12) United States Patent
Hyde et al.

(10) Patent No.: US 10,376,357 B2
(45) Date of Patent: Aug. 13, 2019

(54) INTRAOCULAR LENS SYSTEMS AND RELATED METHODS

(71) Applicant: ELWHA LLC, Bellevue, WA (US)

(72) Inventors: Roderick A. Hyde, Redmond, WA (US); John Marshall, Farnborough (GB); Katherine E. Sharadin, Redmond, WA (US); Clarence T. Tegreene, Mercer Island, WA (US); Lowell L. Wood, Jr., Bellevue, WA (US); Roberto Zaldivar, Mendoza (AR); Roger Zaldivar, Mendoza (AR)

(73) Assignee: ELWHA LLC, Bellevue, WA (US)

( * ) Notice: Subject to any disclaimer, the term of this patent is extended or adjusted under 35 U.S.C. 154(b) by 0 days.

(21) Appl. No.: 15/358,793

(22) Filed: Nov. 22, 2016

(65) Prior Publication Data

US 2017/0071727 A1    Mar. 16, 2017

Related U.S. Application Data

(63) Continuation-in-part of application No. 14/807,673, filed on Jul. 23, 2015, now Pat. No. 9,877,824.

(51) Int. Cl.
*A61F 2/16* (2006.01)
*A61B 5/00* (2006.01)

(52) U.S. Cl.
CPC .......... *A61F 2/1627* (2013.01); *A61B 5/0031* (2013.01); *A61F 2/16* (2013.01); *A61F 2/1654* (2013.01); *A61F 2250/0002* (2013.01)

(58) Field of Classification Search
CPC .... A61F 2/1627; A61F 2/1656; A61F 2/1648; A61F 2/1624; A61F 2/1613
See application file for complete search history.

(56) References Cited

U.S. PATENT DOCUMENTS

| 5,344,447 | A | 9/1994 | Swanson |
| 6,871,951 | B2 * | 3/2005 | Blum ................. G02B 27/017 351/159.03 |
| 7,883,206 | B2 | 2/2011 | Blum et al. |
| 7,926,940 | B2 | 4/2011 | Blum et al. |
| 8,092,016 | B2 | 1/2012 | Blum et al. |
| 8,434,865 | B2 | 5/2013 | Blum et al. |

(Continued)

FOREIGN PATENT DOCUMENTS

| EP | 2 772 791 A1 | 9/2014 |
| WO | WO 2009/153764 A2 | 12/2009 |
| WO | WO 2014/194432 A1 | 12/2014 |

OTHER PUBLICATIONS

European Patent Office, Extended European Search Report, Pursuant to Rule 62 EPC; App. No. EP 16828438.8; dated Feb. 28, 2019 (received by our Agent on Mar. 11, 2019); pp. 1-8.

(Continued)

*Primary Examiner* — Dinah Baria
(74) *Attorney, Agent, or Firm* — Dorsey & Whitney LLP

(57) ABSTRACT

Embodiments disclosed herein are directed to intraocular lens systems having a plurality of materials therein, with at least some of the materials having a diffraction pattern therein and an electrically-modifiable index of refraction collectively configured to selectively alter an effective focal length of the intraocular lens system. Methods of modifying a focal length of an intraocular lens system are also disclosed.

49 Claims, 9 Drawing Sheets

(56) References Cited

U.S. PATENT DOCUMENTS

| | | | |
|---|---|---|---|
| 8,587,734 B2* | 11/2013 | Li | G02C 7/08 349/13 |
| 8,608,800 B2 | 12/2013 | Portney | |
| 9,033,494 B2 | 5/2015 | Blum et al. | |
| 9,155,614 B2 | 10/2015 | Blum et al. | |
| 9,259,309 B2 | 2/2016 | Fehr et al. | |
| 2003/0210377 A1* | 11/2003 | Blum | G02B 27/017 351/159.4 |
| 2003/0231293 A1 | 12/2003 | Blum et al. | |
| 2007/0121065 A1 | 5/2007 | Cox et al. | |
| 2008/0208335 A1 | 8/2008 | Blum et al. | |
| 2008/0218689 A1 | 9/2008 | Blum et al. | |
| 2008/0273169 A1 | 11/2008 | Blum et al. | |
| 2009/0032679 A1 | 2/2009 | Holladay | |
| 2009/0204207 A1 | 8/2009 | Blum et al. | |
| 2010/0002190 A1* | 1/2010 | Clarke | G02C 7/101 351/159.44 |
| 2010/0225834 A1 | 9/2010 | Li | |
| 2010/0324408 A1 | 12/2010 | Klink et al. | |
| 2011/0007266 A1 | 1/2011 | Blum et al. | |
| 2011/0043752 A1 | 2/2011 | Blum et al. | |
| 2011/0285959 A1 | 5/2011 | Gupta et al. | |
| 2012/0140167 A1 | 6/2012 | Blum | |
| 2013/0035760 A1 | 2/2013 | Portney | |
| 2013/0070199 A1 | 3/2013 | Blum et al. | |
| 2013/0073038 A1 | 3/2013 | Azar | |
| 2014/0063464 A1 | 3/2014 | Holladay | |
| 2014/0128941 A1 | 5/2014 | Williams | |
| 2014/0148899 A1 | 5/2014 | Fehr et al. | |
| 2014/0240656 A1 | 8/2014 | Pugh et al. | |
| 2014/0327875 A1 | 11/2014 | Blum et al. | |
| 2015/0205126 A1* | 7/2015 | Schowengerdt | G06T 7/73 345/633 |
| 2015/0362749 A1 | 12/2015 | Biederman et al. | |
| 2015/0378177 A1 | 12/2015 | Blum et al. | |

OTHER PUBLICATIONS

European Patent Office, Extended European Search Report, Pursuant to Rule 62 EPC; App. No. 16828440.4; dated Feb. 22, 2019 (received by our Agent on Mar. 5, 2019); pp. 1-9.

Chinese State Intellectual Property Office, Notification of the First Office Action, App. No. 201680055569.5 (based on PCT/US2016/043068); dated May 7, 2019 (received by our Agent on May 14, 2019); pp. 1-16 (machine translation provided).

Chinese State Intellectual Property Office, Notification of the First Office Action, App. No. 201680055492.1 (based on PCT/US2016/043062); May 7, 2019 (received by our Agent on May 14, 2019); pp. 1-9 (machine translation provided).

European Patent Office, Extended European Search Report, Pursuant to Rule 62 EPC; App. No. EP 16828441.2; Jun. 11, 2019 (received by our Agent on Jun. 10, 2019); pp. 1-9.

* cited by examiner

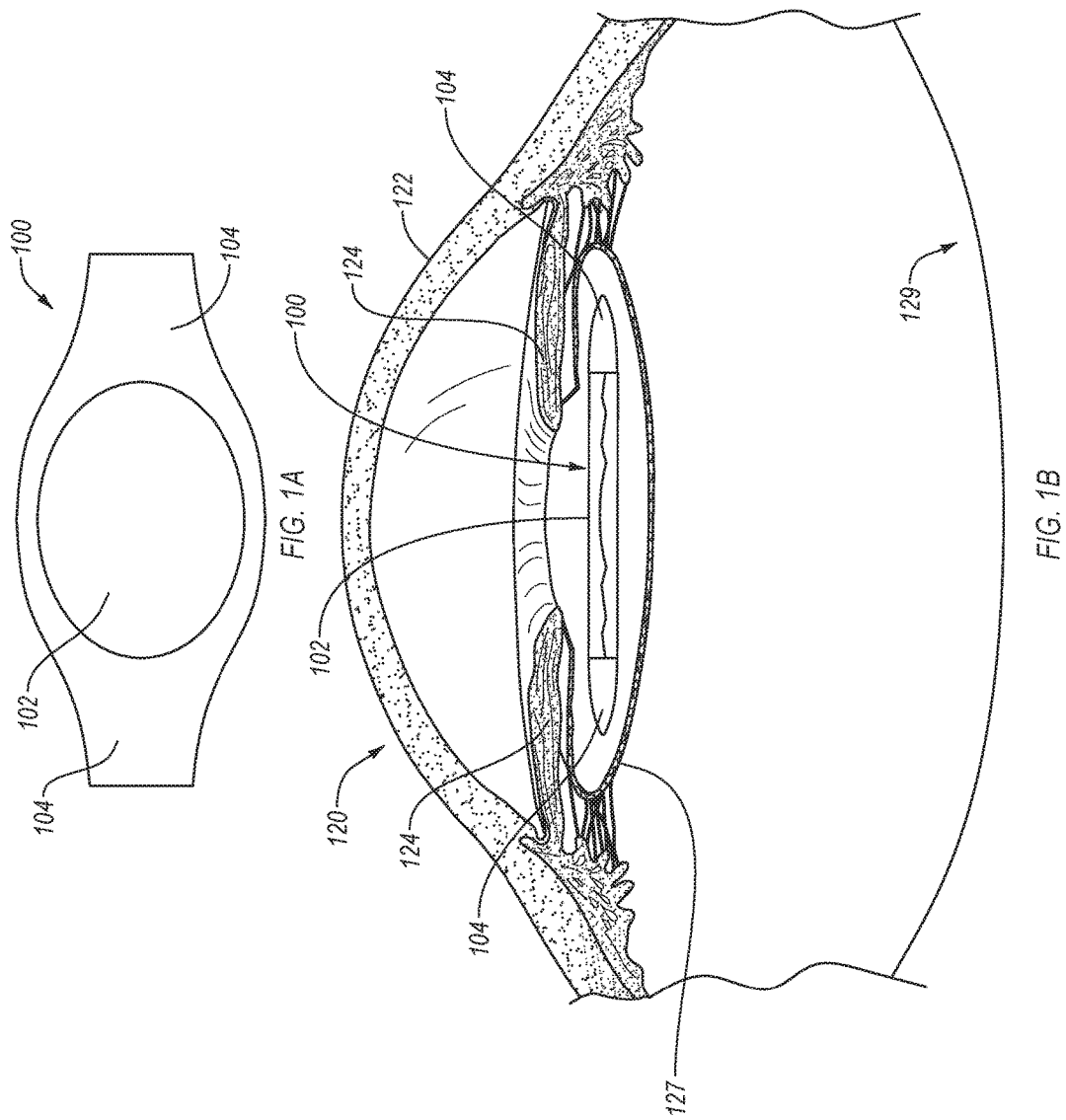

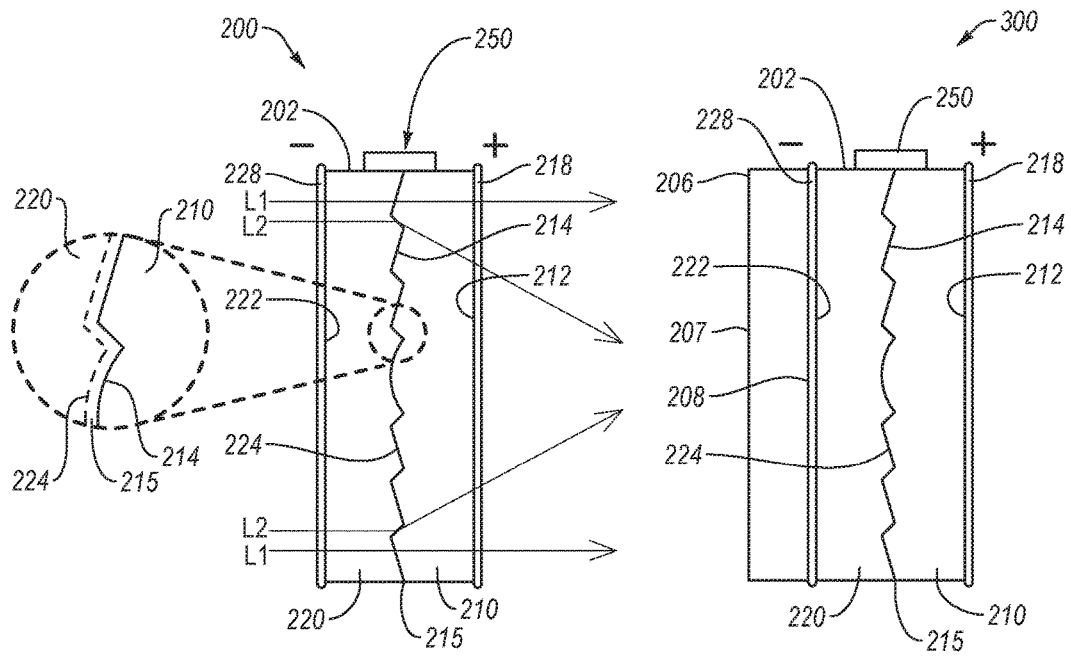
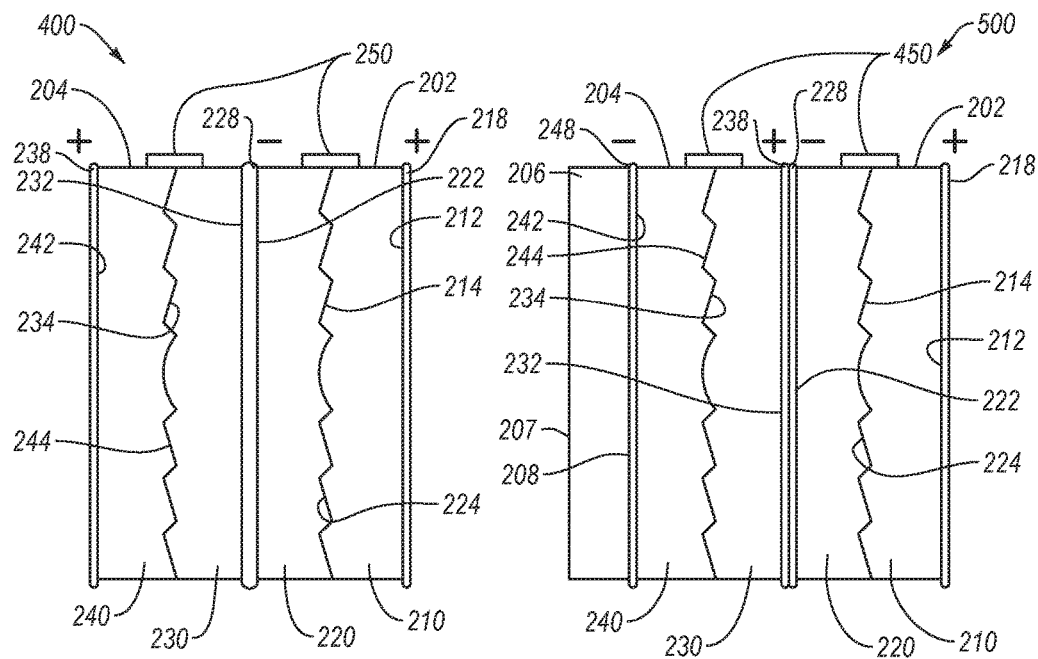

INTRAOCULAR LENS SYSTEMS AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 14/807,673 entitled INTRAOCULAR LENS SYSTEMS AND RELATED METHODS, naming Roderick A. Hyde, John Marshall, Clarence T. Tegreene, Roberto Zaldivar, and Roger Zaldivar as inventors, filed 23 Jul. 2015, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Intraocular lenses ("IOLs"), such as pseudophakic IOLs, aphikic IOLs, or phakic IOLs ("PIOLS"), can be used to correct the vision of a subject. Typical IOLs can include monofocal, multifocal, or accommodative configurations. IOLs can include an optic element (e.g., lens) and haptic elements (e.g., arms or wings configured to aid in positioning the IOL).

Such configurations can be limited to focusing either on near or far vision without selectively modifiable adjustment therebetween. Therefore, manufacturers, users, and designers of IOLs continue to seek improved IOLs.

SUMMARY

Embodiments disclosed herein are directed to IOL systems having a plurality of materials therein, with at least some of the materials having a diffraction pattern and an electrically-modifiable index of refraction collectively configured to selectively alter a focal length of the IOL system. Methods of using such IOL systems are also disclosed.

In an embodiment, an IOL system is disclosed. The IOL system includes a diffractive lens configured to be implanted in an eye of a subject. The diffractive lens includes a first material having an electrically-modifiable first index of refraction, a first outer surface, and a first diffraction surface defining a first diffraction pattern; and a second material having a second index of refraction, a second outer surface remote from and generally opposing the first outer surface of the first material, and a second diffraction surface defining a second diffraction pattern. The second diffraction pattern is substantially complementary to the first diffraction pattern. The IOL system includes a first electrode disposed adjacent to the first outer surface of the first material and a second electrode disposed adjacent to the second outer surface of the second material. The IOL system further includes a controller including control electrical circuitry operably coupled to the first and second electrodes. The controller is configured to bias the first and second electrodes to modify at least the electrically-modifiable first index of refraction of the first material and a focal length of the IOL system.

In an embodiment, a method of modifying a focal length of an IOL is disclosed. The method includes establishing a first effective focal length with an IOL system. The IOL system of the method includes a diffractive lens. The diffractive lens includes a first material having an electrically-modifiable first index of refraction, a first outer surface, and a first diffraction surface defining a first diffraction pattern; and a second material having a second index of refraction, a second outer surface remote from and generally opposing the first outer surface of the first material, and a second diffraction surface defining a second diffraction pattern. The second diffraction pattern is substantially complementary to the first diffraction pattern. The IOL further includes a first electrode disposed adjacent to the first outer surface of the first material and a second electrode disposed adjacent to the second outer surface of the second material. The IOL includes a controller including control electrical circuitry operably coupled to the first and second electrodes, the controller configured to bias the first and second electrodes to modify at least the electrically-modifiable index of refraction of the first material and a focal length of the diffractive lens. The method includes, via the controller, biasing the first and second electrodes to modify at least the electrically-modifiable first index of refraction of the first material and a focal length of the IOL.

In an embodiment, an IOL system is disclosed. The IOL system includes a diffractive lens configured to be implanted in an eye of a subject. The diffractive lens of the IOL system includes a first material having a first outer surface. The diffractive lens of the IOL system includes a second material having a second outer surface remote from and generally opposing the first outer surface, where at least one of the first material or the second material includes an electrically-modifiable index of refraction. The diffractive lens of the IOL system includes an electrically-modifiable diffraction pattern. The IOL system includes a first electrode adjacent to the first material and a second electrode adjacent to the second material. The IOL system includes a controller including a processor, operably coupled to the first and second electrodes, the controller configured to selectively bias one or more of the first and second electrodes effective to modify at least the electrically-modifiable index of refraction, the electrically-modifiable diffraction pattern, and an effective focal length of the intraocular lens system from a first effective focal length to a second effective focal length over a selected duration of time In an embodiment, a method of selectively modifying a focal length of an IOL system is disclosed. The method includes establishing a first effective focal length with an IOL. The IOL system of the method includes a diffractive lens having a first material including a first outer surface and a second material including a second outer surface remote from and generally opposing the first outer surface of the first material, where at least one of the first material and the second material have an electrically-modifiable index of refraction. The diffractive lens of the method includes an electrically-modifiable diffraction pattern. The IOL system of the method includes a first electrode adjacent to the first material and a second electrode adjacent to the second material. The IOL system of the method includes a controller including a processor, operably coupled to the first and second electrodes, the controller configured to bias the first and second electrodes to modify at least the electrically-modifiable index of refraction and a first effective focal length to a second effective focal length. The method includes, via the controller, biasing one or more of the first and second electrodes to modify at least the electrically-modifiable index of refraction effective to cause the diffractive lens to change between the first effective focal length and the second effective focal length over a selected duration of time.

In an embodiment, an IOL system is disclosed. The IOL system includes a diffractive lens configured to be implanted in an eye of a subject. The diffractive lens includes a first material having an electrically-modifiable first index of refraction, a first curved outer surface, and a first curved diffraction surface defining a first diffraction pattern. The diffractive lens includes a second material having a second index of refraction, a second curved outer surface remote from and generally opposing the first outer surface of the first material, and a second curved diffraction surface defining a second diffraction pattern, wherein the second diffraction pattern is substantially complementary to the first diffraction pattern. The IOL system includes a first electrode disposed adjacent to the first material, the first electrode being substantially transparent to visible wavelength light. The IOL system includes a second electrode disposed adjacent to the second material, the second electrode being substantially transparent to visible wavelength light. The IOL system includes at least one sensor configured to detect one or more of a distance between a first focal point and a second focal point, a time of day, an intensity of light in a location of a user of the intraocular lens system, or a color of light in the location of the user. The system includes a controller including a processor operably coupled to the first electrode, the second electrode, and the at least one sensor. The controller is configured to selectively bias one or more of the first or second electrodes effective to modify at least the electrically-modifiable first index of refraction of the first material and an effective focal length of the intraocular lens system from a first effective focal length to a second effective focal length via one or more intermediate focal lengths therebetween over a selected duration of time, responsive to sensed data from the at least one sensor.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1A is a top view of an IOL, according to an embodiment.

FIG. 1B is a side cross-sectional view of an eye having the IOL of FIG. 1A therein.

FIGS. 2-6 are side, cross-sectional views of portions of diffractive lenses of an IOL system according to various embodiments.

DETAILED DESCRIPTION

Figure 6:
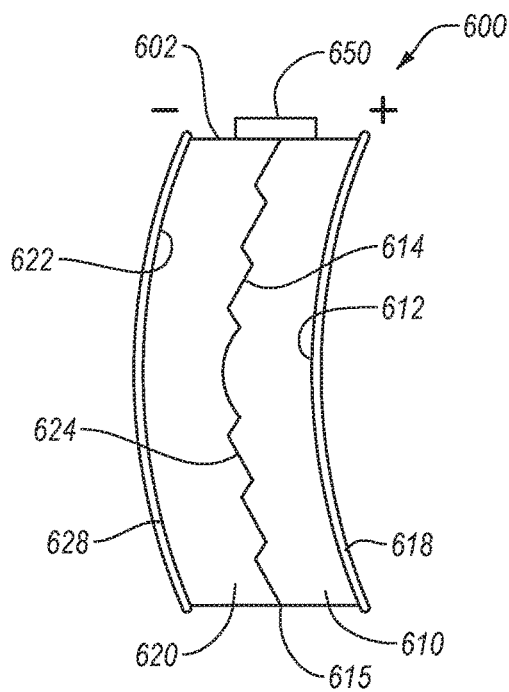

Embodiments disclosed herein are directed to IOL systems having a plurality of materials therein, with at least some of the materials having a diffraction pattern and an electrically-modifiable index of refraction collectively configured to selectively alter a focal length (e.g., an effective focal length) of the intraocular lens system. Methods of using such IOL systems are also disclosed.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The IOLs and systems disclosed herein can provide a selectively modifiable IOL having a selectively modifiable focal length. The IOLs disclosed herein can include a lens and one or more haptics. The lens can include at least one material having an electrically-modifiable index of refraction (including any birefringence associated therewith) and a diffraction surface defining a diffraction pattern therein. The IOLs disclosed herein can change focal length (e.g., effective focal length) by applying a bias or voltage to the at least one material. An IOL can include a first material having an electrically-modifiable index of refraction and a diffraction surface defining a diffraction pattern. The IOL can include a second material having a substantially fixed index of refraction and a diffraction surface, or optionally, an electrically-modifiable index of refraction and a diffraction surface. The first and second materials can interface at their diffraction surfaces (which can be complementary and adjacent to each other), and the diffraction patterns in each are configured to focus light onto the retina of a subject from one or more specific focal lengths. The IOL can include a first electrode adjacent to, in, or on the outer surface of the first material and a second electrode adjacent to, in, or on the outer surface of the second material. The first and second electrodes can provide an electrical bias or voltage across the first and second materials effective to cause any electro-optical material therein to exhibit an altered or modified index of refraction. The modified index of refraction can cause the IOL to exhibit a different focal length, such as shorter or longer than the original or non-activated focal length of the IOL. The focal length can be an effective focal length that can include a combination of fractional percentages of light delivered from different (e.g., discrete) diffractive orders and associated discrete focal lengths. Numerous embodiments are disclosed below, including IOLs having multiple selectively modifiable diffractive lenses, and combination refractive/diffractive lens IOLs.

FIG. 1A is a top view of an IOL 100. The IOL 100 is configured to fit in or on one or more anatomical structures of the eye. The IOL 100 can include a lens 102 and one or more haptics 104. The one or more haptics 104 are physical structures attached to the IOL 100 that hold the IOL 100 in place within the capsular bag within the eye. The lens 102 can be configured to focus light onto the surface of the retina of a subject to improve or correct the vision of a subject. The lens 102 can be substantially circular or elliptical. The lens 102 can include, or be configured as, one or more of a diffractive lens and, optionally, further include a refractive lens. As discussed in more detail below, the lens 102 can be configured as a diffractive lens having a selectively modifiable index of refraction and focal length. The lens 102 can be configured to augment or correct visual deficiencies of a subject or to replace the lens of a subject, such as in cataract surgeries. As shown in FIG. 1A, haptics 104 can be configured as wings extending away from the lens 102. In an embodiment, the haptics 104 can be configured as arms or struts having an elbow or bend therein. The arms can be similar to the wings shown in FIG. 1A with one or more portions of the center of the wings removed therefrom.

FIG. 1B is a side, cross-sectional view of an eye 120 having the IOL 100 implanted therein. The eye 120 can include a cornea 122, an iris 124, a natural lens, and a retina 129 therebehind. One or more IOLs 100 can be implanted in the eye 120. The IOL 100 can be implanted over the natural lens, in front of (e.g., in the anterior chamber) or behind the iris 124 (e.g., in the posterior chamber), or internal to the natural lens such as in the capsular bag 127 of the natural lens. In an embodiment, the eye 120 may not include the natural lens. In such cases, the IOL 100 can replace the natural lens (e.g., can be placed in the anterior chamber, the posterior chamber, or internal to the capsular bag that is used to contain the natural lens). In an embodiment, the haptics 104 can be positioned on one or more structures in the eye 120. For example, the haptics 104 can be positioned on the ciliary body or muscles or in or on a capsular bag 127 of the natural lens. The lens 102 can be located laterally at approximately the midpoint (e.g., center) of the eye 120, with the haptics 104 extending laterally therefrom toward a periphery of the eye. The IOL 100 and, specifically the lens 102, can include one or more materials having a selectively modifiable index of refraction and a diffraction pattern therein. The lens 102 of the IOL 100 is discussed in more detail below.

FIG. 2 is a side, cross-sectional side view of a portion of a diffractive lens of an IOL system 200. The IOL system 200 can be used for cataract surgery, lens replacement, or vision augmentation or correction. The IOL system 200 can include a diffractive lens 202 and a controller 250. The diffractive lens 202 can include one or more materials therein, such as one or more electro-optical materials having an electrically-modifiable index of refraction. The controller 250 can be configured to selectively modify the index of refraction of one or more electro-optical materials in the IOL system 200.

The one or more materials can include a first material 210 and a second material 220. The first material 210 can include an electro-optical material. Electro-optical materials include those materials having an electrically-modifiable index of refraction. Electro-optical materials can be configured to provide a selectively modifiable index of refraction, such as a first, ground state index of refraction and at least a second, activated index of refraction induced by a stimulus (e.g., electrical stimulus applied to an electrically-modifiable material) applied thereto. In an embodiment, one or more electro-optical materials may each include a tunable (e.g., gradient) index of refraction over a specific voltage range, which can include a plurality of selectable focal lengths depending on the voltage applied. The second material 220 can include a substantially electro-optically inert material having a substantially fixed index of refraction. In an embodiment, the second material 220 can include an electro-optical material having a selectively modifiable index of refraction, similar to or different from the index of refraction of the first material 210. The first material can include a first outer surface 212 and the second material can include a second outer surface 222. The first and second outer surfaces 212 and 222 can be remote from one another and positioned in generally opposing directions (e.g., facing away from each other).

The first material 210 can include a first diffraction surface 214 generally opposite to the first outer surface 212 and defining a first diffraction pattern. The second material 220 can include a second diffraction surface 224 generally opposite to the second outer surface 222 and defining a second diffraction pattern. The second diffraction pattern can be substantially complementary (e.g., a mirror image of) to the first diffraction pattern such that the first and second diffraction surfaces 214 and 224 can be substantially seamlessly joined or mated together without any significant gaps therebetween. The first and second materials 210 and 220 can be joined at or meet at an interface 215 therebetween. The interface 215 can include an optically seamless diffraction pattern (e.g., the first and second diffraction patterns joined together) configured to focus light at a specific focal length or point relative to a subject onto a retina of the subject. In general, one fraction of incident light passing through the diffractive patterns will be focused to the specific focal length defined by the index of refraction of the material and diffractive patterns (e.g., defined by the fundamental diffractive order of the patterns), while a second fraction will be un-diffracted and proceed as though the diffractive patterns did not exist. Other (generally smaller) fractions of light will be diffracted to different focal lengths defined by the diffractive patterns (e.g., corresponding to negative or to higher diffractive orders). The relative fractions of incident light which are un-diffracted, diffracted to the specific focal length, and diffracted to the different focal lengths are determined by the depth of the diffraction surfaces and the index of refraction of their materials (e.g., for seamless complementary patterns, by the difference of the index of refraction of the first and second materials 210 and 220). In an embodiment, the first and second materials 210 and 220 may have the same index of refraction, resulting in substantially all incident light being un-diffracted. In an embodiment, the first and second materials 210 and 220 can have different indices of refraction, the value of which can be selected to result in substantially all incident light being diffracted to the specific focal length. Upon activation of the electro-optical material, the index of refraction can change to thereby change the effective focal length of the lens (e.g., to increase the fraction of incident light diffracted to the specific focal length rather than being un-diffracted) in conjunction with one or more diffraction patterns therein. For example, as shown in FIG. 2, the incident light L1 is not diffracted while the IOL system 200 is not activated (e.g., no electrical bias). While the IOL system 200 is activated (e.g., an electrical bias is applied) the incident light L2 can be diffracted due at least in part to the electrically-modified index of refraction of one or more of the first and second materials 210 or 220. In an embodiment, one or more of the first and second materials 210 and 220 can include a tunable index of refraction based on the amount of voltage applied, which can cause the IOL system 200 having the same to exhibit a gradient of focusing power. For example, an IOL having at least one material having a tunable index of refraction can exhibit a first maximum focal length, a second minimum focal length, and a plurality of intermediate focal lengths therebetween, with each of the focal lengths based on the amount of voltage applied to the first and second electrodes 218 and 228. In such embodiments, a generally smooth graduation from a first focal length F1 to a second focal length F2 or a focal length therebetween can be established by gradually increasing or decreasing the electrical bias to the first and second electrodes 218 and 228 until the desired focal length is reached.

In order to provide a sufficient bias (e.g., an electrical voltage) to induce the modified index of refraction in the electro-optical material, the IOL system 200 can include a first electrode 218 and a second electrode 228. The first electrode 218 can be disposed adjacent to, in, or on the first outer surface 212 of the first material 210 and the second electrode 228 can be positioned adjacent to, in, or on the second outer surface 222 of the second material 220. The first and second electrodes 218 and 228 can be configured to deliver or maintain an electrical bias (e.g., electrical field, DC current, or low frequency AC current) across the first and second materials 210 and 220 effective to modify the index of refraction of one or both materials therebetween. Either of the first electrode 218 or the second electrode 228 can be configured as a positive terminal or a negative terminal with the remaining electrode being configured as the counterpart electrode.

The first and second electrodes 218 and 228 can be operably coupled to controller 250 by leads (not shown). As discussed in detail below, the controller 250 can include control electrical circuitry and a power source (e.g., battery) therein. The control electrical circuitry can include a processor operably coupled to a memory storage medium (e.g., a hard drive). The memory storage medium can store one or more of bias amounts, selected durations of time, machine readable instructions for correlating the bias amounts and selected durations of time, characteristic durations of time for one or more materials, one or more machine readable operational programs for applying a bias to one or more of the first and second electrodes over a selected duration of time, etc. The processor can be configured to access and execute one or more machine readable operational programs stored in the memory storage medium. The first and second electrodes 218 and 228 and the controller 250 can form a selectively controllable (e.g., selectively activated) circuit. The control electrical circuitry can be configured to direct the power source to bias the fists and second electrodes 218 and 228.

In an inactivated state, the electro-optical material can exhibit a first index of refraction and, when a bias is applied (e.g., in an activated state), the electro-optical material can exhibit a second or modified index of refraction, different from the first index of refraction. The effective focal point or length of the diffractive lens 202 incorporating the same can be similarly modified. For example, the diffraction patterns of diffractive lens 202 can be configured to provide a number of different focal lengths corresponding to different diffractive orders (e.g., for un-diffracted light, for the fundamental diffractive order or, for other diffractive orders, such as negative or higher diffractive orders). The relative amount of incident light delivered into each different focal length can be dependent upon the index of refraction of the electro-optical material (e.g., whether it is in an inactivated or activated state). For example, when a stronger focus (e.g., near focus) is desired, a bias can be applied across the diffractive lens 202 to modify the index of refraction of one of the first or second materials 210 or 220 therein to provide a focal length nearer the subject than the first focal length associated with the first index of refraction. In an embodiment, the focal length of the diffractive lens 202 (e.g., electro-optical material) without a bias applied thereto is greater than the focal length of the diffractive lens having a bias applied thereto. For example, in a first state embodiment, the first and second materials 210 and 220 have a substantially identical or identical index of refraction. In the first state, the IOL system 200 acts as a single lens having such index of refraction. Incident light is not further deflected by the diffraction pattern. In a second state embodiment, an electrical charge or bias is applied to the IOL system 200 and the index of refraction of the first material 210 is changed. In the second state embodiment, incident light is deflected at the diffraction pattern according to the difference in refractive indices of the first and second materials 210 and 220.

In an embodiment, (e.g., when IOL system 200 also includes a refractive lens or due to corneal focusing) diffractive lens 202 is not the only focusing element in the eye, so that light un-diffracted by the diffraction patterns will be delivered to one focal length (e.g., corresponding to a far focus), while light diffracted at either the fundamental diffractive order or one of the other diffractive orders will be delivered to a second focal length (e.g., corresponding to a near focus).

One or both of the first or second materials 210 or 220 can include an electro-optical material therein (e.g., a material having an electrically-modifiable index of refraction). The electro-optical material can be a solid state material or a liquid crystal material. In some embodiments, the electro-optical material can include a liquid crystal polymer. The electro-optical material can be substantially transparent to visible wavelength light. In an embodiment, the electro-optical material can at least partially filter one or more wavelengths of light, such as one or more wavelengths of visible light. Suitable electro-optical materials can include at least one of lithium niobate, lithium tantalate, lead zirconate titanate, potassium dihydrogen phosphate, cadmium telluride, perovskite lead lanthanum zirconate titanate (PLZT), lead magnesium niobate-lead titanate (PMN-PT) (e.g., $Pb(Mg_{1/3}Nb_{2/3})O_3$—$PbTiO_3$(PMN-PT)), mixtures of any of the foregoing, or any other suitable substantially transparent material having an electrically-modifiable index of refraction.

The second material 220 can include a substantially electro-optically inert material (e.g., having a substantially fixed index of refraction), such as glass; plastic; or other lens materials including one or more of polymethyl methacrylate (PMMA), polypropylene, silicone, polyvinyl fluoride (PVDF), polyamide, polycarbonate, polyimide, hydrophobic acrylics, hydrophilic acrylics, combinations of the foregoing, or any other transparent material suitable for use in an IOL. In an embodiment, the first material 210 includes one or more substantially electro-optically inert materials therein. In an embodiment, each of the first material 210 and the second material 220 includes an electro-optical material such as any of those describe above. In an embodiment, one or both of the first material 210 or the second material 220 includes a solid state or a liquid crystal electro-optical material therein.

In an embodiment, neither the electrode 218 or electrode 228 are located at diffractive surfaces 214 or 224. Instead, for example, the electrode 218 and electrode 228 are located near outer surfaces 212 and 222, respectively. In such an embodiment, the electric field present throughout the first and second materials 210 and 220 can be more uniform (in strength, location, or direction) than in embodiments in which one of the electrodes 218 or 228 is located near the diffractive surface 214 or 224. In an embodiment, this uniformity can be utilized when a solid state electro-optic material is used for first material 210 or second material 220. In such embodiments, this electrode configuration can enable the diffractive lens to use solid state materials in a linear portion of their index-vs-field response curve, as opposed to use of liquid crystal materials in a saturated index-vs-field regime. In an embodiment, the second material 220 is selected so that its DC dielectric constant substantially matches the DC dielectric constant of first material 210, so that the thickness and slope variations caused by the interface between diffractive surfaces 214 and 224 do not cause substantial local variations in the electric field's uniformity (and hence in the refractive index of electro-optically active material 210 or 220).

The diffraction patterns of the first and second diffraction surfaces 214 and 224 can be configured to focus or converge the light from a specific focal length onto the retina of a subject without inducing significant interference (e.g., at the prismatic effect) at the retina. The diffraction pattern (e.g., diffraction grating or lens, digitally or continuously brazed profile) can be formed in one or both of the first material 210 or the second material 220 first, with the second material 220 or first material 210 being molded thereto or therein. For example, the diffraction pattern can be formed in the first material 210 and the second material 220 can be poured/molded onto the first material so that the second material 220 substantially conforms or is complementary to the diffraction pattern in the first material 210. The diffraction pattern can be defined by a spatial variation in a thickness of one or both of the first or second materials 210 or 220. In an embodiment, changing the spatial variation in the thickness of one or both of the first or second materials 210 or 220 can provide or eliminate apodization in the images focused therethrough. In an embodiment, an apodized or unapodized spatial variation in the thickness of one or more materials can be used. In an embodiment, both of the first diffraction surface 214 and the second diffraction surface 224 can have the corresponding or complementary diffraction patterns formed therein (e.g., each having a pattern exhibiting substantially identical spatial periodicity), and the first and second materials 210 and 220 are fitted together to form a substantially unitary lens structure. In an embodiment, the first diffraction surface 214 and the second diffraction surface 224 can have different diffraction patterns (e.g., exhibiting substantially different spatial periodicity) formed therein, and the first and second materials 210 and 220 include another material therebetween having complementary surface configurations to the diffraction patterns (e.g., forming an interface having substantially identical spatial periodicity to each individual diffraction surface) in the first diffraction surface 214 and the second diffraction surface 224. The first material 210, the second material 220, and the another material can fit substantially seamlessly together to form a substantially unitary lens structure. Suitable diffraction patterns can include a Fresnel pattern (e.g., defining a Fresnel lens), a linear pattern (e.g., defining a diffraction grating), or any other pattern suitable for inducing diffraction (e.g., lens combined with grating, lens with aberrational corrections, etc.). Suitable diffraction patterns can include any number of steps therein, such as 10 or more, about 10 to about 1000, about 50 to about 500, about 100 to about 300, about 20 to about 250, or less than about 500 steps. The steps can include a step height of at least about 0.2 µm, such as about 0.5 µm to about 20 µm, 1 µm to about 10 µm, or less than about 50 µm. The step height, multiplied by the refractive index jump across the step (e.g., the index difference between the first material 210 and the second material 220) can define one wavelength of light (e.g., 550 nm) or multiple wavelengths. The steps can include a step length (e.g., diffractive period) of at least about 0.5 µm, such as about 1 µm to about 100 µm, about 5 µm to about 50 µm, about 1 µm to about 10 µm, or less than about 200 µm, the value being dependent upon the desired focal length and the number of wavelengths defined by the step height. The step profile or variation of step height versus lateral distance within each step length can be digitally or continuously blazed. Digitally blazed profiles can include a single step within each period, or multiple steps (e.g., 4 sub-steps of different step heights); while continuously blazed profiles can be linear ramps ("sawtooth" profiles), sections of parabolas, or other shapes.

The average axial thickness of the first or second materials 210 or 220 can vary depending on the materials used, the desired refractive or diffractive properties of the lens, the desired correction to the vision of a subject, or any other suitable criteria. The average thickness (e.g., including any ridges or grating) of the first or second material 210 or 220 can be at least about 0.5 µm, such as about 1 µm to about 3 mm, about 100 µm to about 2 µm, about 500 µm to about 1 mm, about 250 µm to about 2 µm, or about 1.5 mm. The average thickness of the first and second materials 210 and 220 can be identical or substantially different. In an embodiment, one or more portions of one or more of the first and second materials 210 or 220 can be substantially planar. For example, the first outer surface 212 and the second outer surface 222 can be substantially planar, such as in parallel to one another. As discussed in more detail below, one or more portions of the first and second materials 210 and 220 can be substantially non-planar (e.g., curved) and parallel or non-parallel to each other. In an embodiment where the first and second materials 210 and 220 include at least one non-parallel curved surface, the curvature of the non-parallel surfaces can form a refractive lens.

The first and second electrodes 218 and 228 can be configured to limit distortion of the visual quality of the IOL system 200 at the retina. For example, one or both of the first and second electrodes 218 and 228 can include a material substantially transparent to one or more wavelengths of visible light (e.g., substantially transparent to all visible light) or can be sufficiently thin to substantially limit any refractive or diffractive effects therefrom. In an embodiment, one or both of the first or second electrodes 218 or 228 can include a transparent conducting material. Suitable transparent conducting materials can include one or more of indium-tin-oxide; aluminum-doped zinc-oxide; indium-doped cadmium-oxide; or a transparent conductive polymer such as poly(3,4-ethylenedioxythiophene), Poly(3,4-ethylenedioxythiophene):poly(styrene sulfonate), or Poly(4,4-dioctylcyclopentadithiophene). In an embodiment, the first and second electrodes 218 and 228 can be about 0.05 µm thick or more, such as about 0.05 µm to about 500 µm, about 0.1 µm to about 200 µm, about 0.5 µm to about 100 µm, about 1 µm to about 50 µm, about 0.05µ to about 100 µm, about 1 µm to about 500 µm, or about 10 µm thick.

The first and second electrodes 218 and 228 can be configured to complement the surface geometry of one or more surfaces of the first and second materials 210 and 220. For example, one or both of the first and second electrodes 218 or 228 can be configured as substantially planar or curved to match the first outer surface 212 or the second outer surface 222.

In an embodiment, the overall or maximum thickness of the IOL system 200, including the diffractive lens 202 and the electrodes 218 and 228, can be at least about 10 µm. For example, the overall or maximum thickness can be about 10 µm to about 6 mm, about 500 µm to about 5 mm, about 100 µm to about 1.5 mm, about 250 µm to about 3 mm, about 1 mm to about 4 mm, about 3 mm to about 5 mm, about 4.5 mm to about 5.5 mm, about 2 mm, about 3 mm, or about 4 mm.

In an embodiment, the diffractive lens 202 of the IOL system 200 can be configured as a Fresnel lens having surface geometry configured to provide a sharp image to the retina (e.g., imaging Fresnel lens). The Fresnel lens can provide relatively greater optical and physical thickness than other types of diffractive lenses such as, corresponding to a high-order (e.g., $5^{th}$ order, $10^{th}$ order, $20^{th}$ order, etc.) diffraction profile and hence a greater number-of-optical-wavelengths of thickness. In an embodiment, the first material 210 can be configured as a Fresnel lens and the second material 220 can be configured with a substantially complementary surface to interface therewith. The first material 210 (e.g., Fresnel lens) or in some cases, the second material 220, may each be formed from an electro-optical material or a substantially inert material, which may have a substantially similar or identical dielectric constant to allow substantially uniform voltage across the entire lens 202. In an embodiment, the first material 210 can include a first electro-optical material and the second material 220 can include a second electro-optical material having identical or different indices of refraction or dielectric constants. Depending on the diffraction blazing and geometric patterning of the Fresnel lens, the IOL may exhibit a series of potential focal lengths substantially in a gradient with the effective focal length dependent upon the amount of electrical bias thereacross. For example, when an electro-optical material formed as a Fresnel lens includes a sufficient blazing and geometric patterning, the IOL system 200 may be able to focus different orders of light onto the retina of a subject, thereby allowing a substantially continually graduating focal length dependent upon the amount of voltage applied across the electro-optical material.

FIG. 3 is a side, cross-sectional view of a portion of a lens of an IOL system 300 according to an embodiment. The IOL system 300 can be configured substantially identical or similar to the IOL system 200, with like parts having like numbering. The IOL system 300 can include the diffractive lens 202 and a refractive optical element 206 (e.g., refractive lens) associated with and positioned optically in series with the diffractive lens 202. The refractive optical element 206 can comprise the second material as employed in the diffractive lens 202, or can comprise another optical material. The IOL system 300 includes the first material 210 and the second material 220. The first material 210 and the second material 220 include the first outer surface 212 and the first diffraction surface 214, and the second outer surface 222 and the second diffraction surface 224, respectively. The IOL system 300 includes the first electrode 218 and second electrode 228. The IOL system 300 further includes the controller 250 operably coupled to the first and second electrodes 218 and 228. The IOL system 300 can include a refractive optical element 206 (e.g., refractive lens) in series with the diffractive lens 202. For example, as shown in FIG. 3, the refractive optical element 206 can be in series with the diffractive lens 202 and positioned adjacent to the second outer surface 222 of the second material 220. The refractive optical element 206 can include one or more surfaces, such as outer surface 207 and interfacing surface 208.

The interfacing surface 208 can interface with the diffractive lens 202 adjacent to the second outer surface 222. The interfacing surface 208 can have a complementary configuration (e.g., parallel) to the second outer surface 222, such that the interfacing surface 208 remains in contact with the second outer surface 222 across substantially the entire second outer surface 222. In an embodiment, the interfacing surface 208 can interface with the diffractive lens 202 at the second electrode 228 (e.g., the second electrode 228 is interposed between the interfacing surface 208 and the second outer surface 222). In an embodiment, the interfacing surface 208 can interface with the diffractive lens 202 at the second outer surface 222, and the second electrode 228 can be disposed adjacent to the outer surface 207 of the refractive optical element 206.

The outer surface 207 can be substantially parallel to the interfacing surface 208 or can exhibit a non-parallel curvature resulting in a desired refraction. In an embodiment, one or both of the outer surface 207 or the interfacing surface 208 can exhibit a curvature (e.g., concave or convex). The curvature of one or both of the outer surface 207 or the interfacing surface 208 can be substantially parallel or non-parallel to each other, resulting in a desired refraction. The curvature of one or both of the outer surface 207 or the interfacing surface 208 can be substantially parallel or non-parallel to one or more surfaces of the diffractive lens 202, resulting in a desired refraction. In an embodiment, the second material 220 can be at least partially configured as a refractive lens (e.g., having a curvature configured to refract light in a selected manner). In such embodiments, the second electrode 228 can be disposed adjacent to a surface of the refractively configured second material 220. As used herein, "curved" or "curvature" in conjunction with materials having a diffractive surface therein includes the average thickness of a material over the periodicity of any diffraction patterns therein (e.g., curvature does not include fine-scale peaks and valleys of the diffraction pattern).

In an embodiment, the refractive optical element 206 can be disposed adjacent to the first outer surface 212 of the first material 210 in a similar or identical manner as described above with respect to the second outer surface 222 of the second material 220. In an embodiment, more than one refractive optical element 206 can be disposed adjacent to the diffractive lens 202. For example, the one or more refractive optical elements 206 can be positioned optically in series with the diffractive lens 202 adjacent to the first outer surface 212 and the second outer surface 222. The one or more refractive optical elements 206 can include an electro-optical material or an electro-optically inert material therein. For example, the refractive optical element 206 can include an electro-optically inert material therein (e.g., an electro-optically inert material employed as the second material 220 of the diffractive lens 202), such that the refractive optical element 206 has a substantially fixed index of refraction.

In an embodiment, the refractive optical element 206 can be interposed between the first material 210 and the second material 220. The refractive optical element 206 can include diffraction patterns generally matching the first diffraction pattern and the second diffraction pattern such that the refractive optical element 206 can be substantially seamlessly interposed between the first and second materials. The refractive optical element 206 interposed between first and second materials 210 and 220 can be an electrically conductive material or an electrically insulating material. In an embodiment, the refractive optical element 206 can serve as an electrical insulator such that a bias applied to the first and second electrodes 218 and 222 adjacent thereto also extends through the refractive optical element. In an embodiment, the refractive optical element 206 having an electrically conducting material can be configured to serve as an electrode, such as the first electrode 218 or second electrode 228. The refractive optical element 206 interposed between the first and second elements 210 and 220 can have curved surfaces matching those curves of the surfaces to which they are adjacent. The refractive optical element 206 interposed between first and second materials 210 and 220 can have curved surfaces of slightly different curvatures forming a refractive lens.

The controller 250 can be used to apply a bias to the first and second electrodes 218 and 228 sufficient to alter the index of refraction of one or more of the first material 210, the second material 220, or in an embodiment, the refractive optical element 206.

In an embodiment, a diffractive lens system can include a first diffractive lens and at least one additional diffractive lens similar to or different from the first diffractive lens. FIG. 4 is a side, cross-sectional view of a portion of a lens of an IOL system 400 according to an embodiment. The IOL system 400 includes a first diffractive lens 202, a second diffractive lens 204 in optical series with the first diffractive lens 202, and one or more controllers 250 configured to apply an electrical bias thereto. The first diffractive lens 202 can be similar or identical to the diffractive lens described above with respect to FIG. 2, including any components thereof. For example, the first diffractive lens 202 can include the first material 210 having the first outer surface 212 and the first diffraction surface 214; the second material 220 having the second outer surface 222 and the second diffraction surface 224; the first electrode 218 adjacent to the first outer surface 212; the second electrode 228 adjacent to the second outer surface 222; and the controller 250 configured to apply a bias therebetween, substantially as described above. The IOL system 400 can further include a second diffractive lens 204, such as in series with the first diffractive lens 202. The second diffractive lens 204 can include one or more components similar or identical to the components of the first diffractive lens 202.

The second diffractive lens 204 can include a third material 230 and a fourth material 240. The third material 230 can include a third outer surface 232 and a third diffraction surface 234 substantially opposite thereto and defining a third diffraction pattern. The fourth material 240 can include a fourth outer surface 242 and a fourth diffraction surface 244 substantially opposite thereto and defining a fourth diffraction pattern. The fourth diffraction pattern can be substantially complementary to the third diffraction pattern such that when the third and fourth diffraction surfaces 234 and 244 are joined they have a substantially seamless (e.g., no gaps or voids) interface therebetween.

The second diffractive lens 204 can include one or more electrodes operably connected thereto. For example, the diffractive lens 204 can be operably coupled to one of the first electrode 218 such as when the fourth outer surface 242 is adjacent to the first outer surface 212, or, as shown, to the second electrode 228 such as when the third outer surface 232 is adjacent to the second outer surface 222. The second diffractive lens 204 can include one or more electrodes distinct from the first and second electrodes. For example, the second diffractive lens 204 can include a third electrode 238 disposed on or adjacent to the fourth outer surface 242. The third electrode 238 can include a material, configuration, thickness, or placement similar or identical to those described above for the first and second electrodes 218 and 228. For example, the third electrode 238 can include a transparent conductive material configured to limit any effect on the transmission of light therethrough.

In an embodiment, the third material 230 can include identical or similar material compositions, diffraction patterns, thicknesses, or any other characteristic of the first material 210 described herein. In an embodiment, the fourth material 240 can include identical or similar material compositions, diffraction patterns, thicknesses, or any other characteristic of the second material 220 described herein. For example, the third material 230 can include an electro-optical material and the fourth material 240 can include an electro-optically inert material or an electro-optical material as disclosed above with respect to the first and second materials 210 and 220.

The third material 230 or fourth material 240 can be configured differently than the first and second materials 210 and 220 respectively. In an embodiment, the third and fourth materials 230 and 240 can include a material composition, diffraction pattern, thickness, or any other characteristic different from the first and second materials 210 and 220. For example, the third and fourth materials 230 and 240 can include a diffraction pattern different from the first and second materials 210 and 220, such that application of an electrical bias across the third and fourth materials 230 and 240 results in a different focal length for the IOL system 400 than a bias applied across the first and second materials 210 and 220.

In an embodiment, the index of refraction of each of the first, second, third, and fourth materials 210-240 can be the same or different than one or more of the other first, second, third, and fourth materials 210-240. For example, the electro-optical material of the first material 210 can have a different electrically-modifiable index of refraction than the electro-optical material of the third material 230, in one or more of the ground and activated states. In an embodiment, the third and fourth materials 230 and 240 can include an electro-optical material or electro-optically inert material having a different index of refraction than the first and second materials 210 and 220, such that application of an electrical bias across the third and fourth materials 230 and 240 results in a different focal length for the IOL system 400 than a bias applied across the first and second materials 210 and 220.

The IOL system 400 can include one or more controllers 250 operably coupled to the first electrode 218, the second electrode 228, or the third electrode 238. In an embodiment, a first controller 250 can be operably coupled to the first electrode 218 and the second electrode 228, either directly or indirectly through electrical leads (not shown). The first controller 250 can include a power supply and control electrical circuitry configured to direct the power source to apply an electrical bias between the first and second electrodes 218 and 228 sufficient to alter the index or refraction of any electro-optical material (e.g., first material 210) therebetween. In an embodiment, the second diffractive lens 204 can be disposed adjacent to the second outer surface 222, as shown. In an embodiment, a second controller 250 can be operably coupled to the second electrode 228 and the third electrode 238 either directly or indirectly through electrical leads (not shown). The second controller 250 can include a power supply and control electrical circuitry configured to direct the power source to apply an electrical bias between the second and third electrodes 228 and 238 sufficient to alter the index or refraction of any electro-optical material therebetween (e.g., the third material 230). In such an embodiment, the first and second controllers 250 can each be operably coupled to the second electrode 228 but be configured as separate circuits each including the first and third electrodes 218 and 238, respectively, and each capable of being operated independently by each controller 250.

In an embodiment (not shown), the second diffractive lens 204 can be disposed adjacent to the first outer surface 212. In such an embodiment, the first controller 250 can be similar or identical as described above and the second controller 250 can be operably coupled to the first electrode 218 and the third electrode 238 either directly or indirectly through electrical leads. The second controller 250 can include a power supply and control electrical circuitry configured to direct the power source to apply an electrical bias between the second and third electrodes 228 and 238 sufficient to alter the index or refraction of any electro-optical material therebetween (e.g., the third material 230). In such an embodiment, the first and second controllers 250 can each be operably coupled to the first electrode 218 but be configured as separate circuits each including the second and third electrodes 228 and 238, respectively, and each capable of being operated independently by each controller 250. The controllers 250 can be operated independently to selectively alter the index of refraction of one or more electro-optical materials in the IOL system 400 to provide one or more differing focal lengths thereto. While depicted as having more than one controller 250, the IOL system 400 can be configured with only one controller 250 operably coupled to each of the first, second, and third electrodes 218-238. In such embodiments, the single controller 250 can be configured to independently operate the first and second electrodes 218 and 228, and the first and third electrodes 218 and 238 or second and third electrodes 228 or 238 depending on the series arrangement of the first diffractive lens 202 and the second diffractive lens 204.

In an embodiment, rather than sharing one or more electrodes between adjacent diffractive lenses as described above with respect to IOL system 400, an IOL can include a fourth electrode operably coupled to the second diffractive lens. FIG. 5 is a side, cross-sectional view of an IOL system 500 having four electrodes forming two separate circuits, according to an embodiment. In an embodiment, the first and second electrodes 218 and 228 can be operably coupled to the first and second outer surfaces 212 and 222 of the first and second materials 210 and 220. In an embodiment, the IOL system 500 can include a third electrode 238 and a fourth electrode 248 operably coupled to the third and fourth outer surfaces 232 and 242 of the third and fourth materials 230 and 240, respectively.

The third or fourth electrodes 238 or 248 can be configured similar or identical to the first and second electrodes 218 or 228, including any material, thickness, position, or other property described herein. For example, the third and fourth electrodes can be configured as a thin layer of an electrically conductive transparent material matching the contours of the surface to which it is attached. In an embodiment, the third and fourth electrodes 238 and 248 can be parallel to each other. In an embodiment, the third and fourth electrodes 238 and 248 can be configured to differ from the first and second electrodes 218 and 228 by one or more of any material, thickness, position, or other property associated therewith. In an embodiment, the first electrode 218 and the third electrode 238 can be configured as positive electrodes and the second electrode 228 and the fourth electrode 248 can be configured as negative electrodes, or vice versa. In an embodiment, a transparent insulating material can be disposed between the second and third electrodes 228 and 238 or the first and fourth electrodes 228 and 248 when positioned adjacent to one another. The transparent insulating material can limit or prevent electrical leakage between the electrodes and unwanted partial activation of the electro-optical materials associated with the electrode not being selectively activated. Suitable transparent insulating material can include acrylic or polycarbonate materials.

The first and second electrodes 218 and 228 can be operably coupled to a controller 250 and the third and fourth electrodes can be operably coupled to a controller 250, such as the same controller 250 or a separate controller 250. The controller 250 can be configured to selectively operate the first and second electrodes 218 and 228 and the third and fourth electrodes 238 and 248 to independently provide an electrical bias sufficient to alter the electrically-modifiable index of refraction of a material therebetween (e.g., the third material 230) and the focal length of the IOL system 500.

In an embodiment, one or more refractive optical elements (e.g., refractive lens) can be positioned optically in series with one or more diffractive lenses. FIG. 5 is a side, cross-sectional view of a lens of the IOL system 500 having diffractive lenses 202 and 204 as described above with respect to IOL system 400 and further including the refractive optical element 206 in series therewith. The refractive optical element 206 of the IOL system 500 can be similar or identical to the refractive optical element described above with respect to IOL system 300. For example, the refractive optical element 206 can include a material separate and distinct from the first, second, third, or fourth materials 210-240. The refractive optical element 206 can include a material such as an electro-optical material or an electro-optically inert material. The refractive optical element 206 can be positioned in series with the first and second diffractive lenses 202 and 204 adjacent to the fourth outer surface 242 as shown, adjacent to the first outer surface 212, or interposed between the first and second lenses 202 and 204. In such an embodiment, the outer surface 207 of the refractive optical material 206 can be disposed adjacent to the second or third outer surface 222 or 232 of the second or third materials 210 or 220 and the interfacing surface 208 can be disposed adjacent to the other of the second or third outer surface 222 or 232. In an embodiment, more than one refractive optical element 206 can be disposed in series with more than one diffractive lens. In an embodiment, the first diffractive lens 202 can be configured with a first curve and the second diffractive element can be planar or have a different curvature than the first curve. One or more of the surfaces 207 or 208 of the refractive optical element 206 associated therewith can be curved or planar to match the surface geometry of one or more of the surfaces of the diffractive lenses adjacent thereto. In an embodiment, the refractive optical element 206 can include differing curvatures on the outer surface 207 and the interfacing surface 208 such that the refractive optical element 206 provides and additional refractive property to the IOL system associated therewith. In an embodiment, the refractive optical element can include one or more of the first, second, third, or fourth materials 210-240. For example, one or more of the first, second, third, or fourth materials 210-240 can include a curved outer surface or a curved diffraction surface, resulting in refraction.

FIG. 6 is a side, cross-sectional view of a portion of a lens of an IOL system 600 having a curved diffractive lens 602, according to an embodiment. The IOL system 600 can be configured substantially identical or similarly as the IOL system 200, with like parts having like numbering. For example, the IOL system 600 can include a diffractive lens 602 and a controller 650. The diffractive lens 602 can be similar or identical to the diffractive lens 202 or 204 described above, including any components or properties thereof. For example, the diffractive lens 602 can include the first material 610 having the first outer surface 612 and the first diffraction surface 614; the second material 620 having the second outer surface 622 and the second diffraction surface 624; the first electrode 618 adjacent to the first outer surface 612; the second electrode 628 adjacent to the second outer surface 622; and the controller 650 configured to apply a bias therebetween, substantially as described above. One or more of the first material 610, first outer surface 612, first diffraction surface 614, the second material 620, second outer surface 622, and second diffraction surface 624, the first electrode 618; the second electrode 628, or the controller 650 can be configured to have one or more properties similar or identical to the corresponding, diffractive lens 202, first material 210, first outer surface 212, first diffraction surface 214, the second material 220, second outer surface 222, and second diffraction surface 224, the first electrode 218, the second electrode 228, and the controller 250 described above.

The diffractive lens 602 can include the first material 610 having a first outer surface 612 and a first diffraction surface 614. One or more of the first outer surface 612 or first diffraction surface 614 can include a curvature therein. The diffraction pattern in the diffraction surface of the materials having curved surfaces can be configured to diffract light in concert with the curved configuration. In an embodiment, the curvature of the first outer surface 612 can be similar or identical to the curvature of the first diffraction surface 614 (e.g., the averaged curvature of the first diffraction surface ignoring the peaks and valleys of the diffraction pattern therein) such that the first material causes light passing therethrough to bend at least partially based on the curvature therein. For example, the curvature of the first outer surface 612 can be substantially parallel to the curvature of the first diffraction surface 614. In an embodiment, the curvature of the first outer surface 612 can be different than the curvature of the first diffraction surface 614 such that the first material 610 causes light passing therethrough to refract at least partially based on each of the curvatures therein.

The second material 620 can include a second outer surface 622 and a second diffraction surface 624. One or more of the second outer surface 622 or second diffraction surface 624 can include a curvature therein. In an embodiment, the curvature of the second outer surface 622 can be similar or identical to the curvature of the second diffraction surface 624 (e.g., the average curvature of the second diffraction surface ignoring the peaks and valleys of the diffraction pattern therein). For example, the curvature of the second outer surface 622 can be substantially parallel to the curvature of the second diffraction surface 624. In an embodiment, the curvature of the second outer surface 622 can be different than the curvature of the second diffraction surface 624 such that the second material 620 causes light passing therethrough to refract at least partially based on the curvature therein. In an embodiment, the curvature of the second outer surface 622 can be different than the curvature of the first outer surface 612 such that the first material 610 and the second material 620 causes light passing therethrough to refract at least partially based on the curvature therein. In an embodiment in which diffractive lens 602 includes non-parallel surfaces (e.g., the outer surfaces 622 and 612, the first material surfaces 612 and 614, and/or the second material surfaces 622 and 624) such that light passing therethrough is at least partially refractive, diffractive lens 602 has both diffractive and refractive optical power and can function as a joint refractive-diffractive lens.

In an embodiment, one or more of the first outer surface 612, the first diffraction surface 614, the second outer surface 622, or the second diffraction surface 624, can include any one of a planar configuration, a concave curve, a convex curve, a compound concave or convex curve, or combinations thereof. For example, as shown, the first outer surface 612 can exhibit a concave curve, the second outer surface can exhibit a convex curve therein, the first diffraction surface 614 can exhibit a convex curve therein, and the second diffraction surface 624 can exhibit a concave curve therein. In an embodiment, the curvature of the first outer surface 612 can be similar or identical to the curvature of the second outer surface 622, such as substantially parallel thereacross. In an embodiment, the convex curvature of the first outer surface 612 can be slightly different from the convex curvature of the second outer surface 622 and configured to provide specific bend (e.g., focal length) to the light passing therethrough.

In an embodiment, the curvature of the first outer surface 612 can be different from the curvature of the second outer surface 622, thereby forming a refractive lens. For example, the first outer surface 612 can include convex curvature and the second outer surface 622 can include a convex curvature different from the first outer surface 612, a concave curvature, or planar configuration. In an embodiment, any surface of the first material 610 or the second material 620 can exhibit a different or identical geometry to one or more of the other surfaces of the first material 610 or the second material 620.

In an embodiment, the curvature of the first diffraction surface 614 (e.g., average curvature of the material ignoring any peaks or valleys of the periodicity therein) can be substantially complementary to the curvature of the second diffraction surface 624 such that the first and second diffraction surfaces fit seamlessly together to form a unitary lens at an interface 615 therebetween. In an embodiment, the curvature of the first diffraction surface 614 can be non-complementary to the curvature of the second diffraction surface 624 such that an intermediate material may be between the first and second diffraction surfaces to provide in interface 615 sufficient to create a seamless unitary lens.

In an embodiment, the first and second electrodes 618 and 628 can include a geometry configured to match the surface on which they are disposed. For example and as shown, the first electrode 618 can have a concave curvature corresponding to the concave curvature of the first outer surface 612 and the second electrode 628 can have a convex curvature corresponding to the convex curvature of the second outer surface 622.

In an embodiment, an IOL system can include an additional diffractive lens having one or more surfaces including surface geometry (e.g., curvature or planar configurations) complementary, similar, or identical to the first outer surface, second outer surface, first diffraction surface, or second diffraction surface disclosed above. In an embodiment, the first lens can be configured as a refractive lens and the second lens can be configured as a refractive lens, each having a complementary or slightly different curvature therein. The first diffractive lens can have a different curvature from the second diffractive lens such that the combination of the first and second diffractive lenses creates a refractive optical element or lens.

Figure 7:
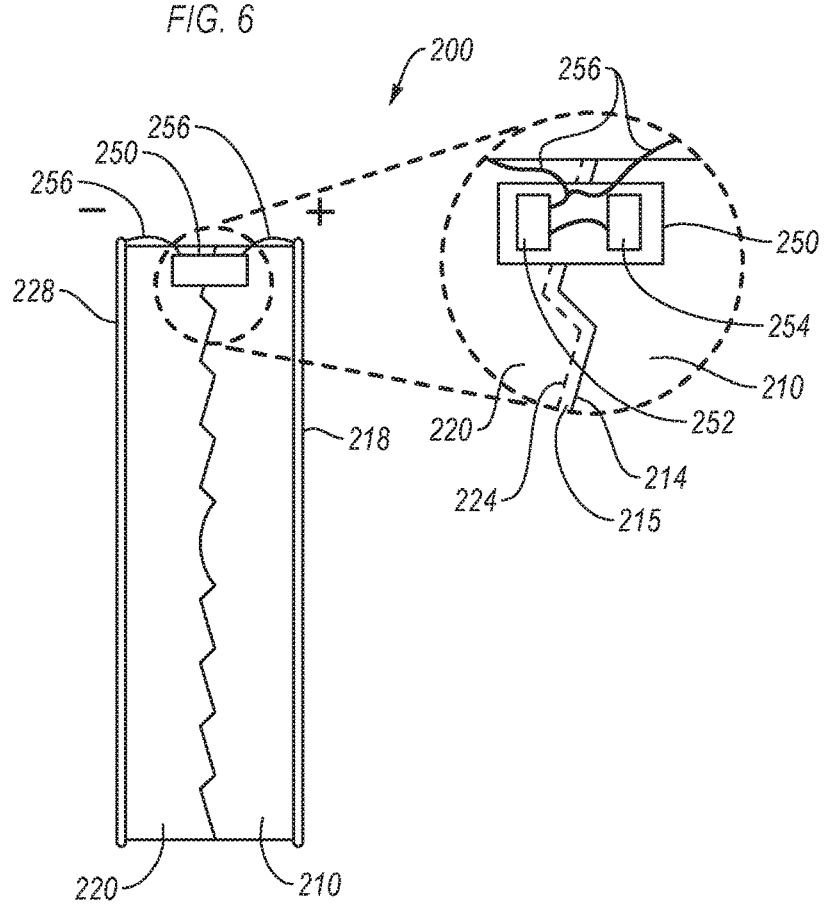
FIG. 7 is a cross-sectional side view of a portion of the diffractive lens of an IOL system including a schematic diagram of a controller associated therewith, according to an embodiment.

FIG. 7 is a side, cross-sectional view of a portion of a lens of the IOL system 200 including a schematic view of the controller 250, according to an embodiment. The controller 250 can be disposed within one or more of the haptic or the lens of an IOL. In an embodiment, the controller 250 can be at least partially embedded within the lens 202 of the IOL system 200. The controller 250 can include a power source 252 and control electrical circuitry 254 operably coupled thereto. The control electrical circuitry 254 can be configured to direct the power source 252 to apply a bias or voltage to one or more electrodes operably coupled thereto. The one or more electrodes can be operably coupled to the controller 250 or the power source 252 via one or more electrical leads 256. The electrical leads 256 can be at least partially embedded within the diffractive lens 202 or the haptic of an IOL. The controller 250 or the electrical leads 256 can be disposed at a periphery of the diffractive lens 204 or IOL so as not to interfere with the vision of a subject. The controller 250 or the electrical leads 256 can be positioned within one or more cavities formed in the interfacing surfaces of the first and second materials 210 or 220. In an embodiment, the controller 250 or the electrical leads 256 can be disposed entirely within one of the first material 210 or the second material 220, such as embedded within one or more cavities therein. In an embodiment, one or more of the controller 250, the power source 252, the control electrical circuitry, or the electrical leads 256 can be disposed externally to the diffractive lens such as on a surface thereof, or on an electrode associated therewith. In an embodiment, the electrical leads or the controller can be encased in a transparent insulating material (e.g., acrylic or polycarbonate) configured to prevent electrical leakage therefrom.

In an embodiment, the power source 252 can be configured to deliver an electrical bias to one or more electrodes or one or more circuits including one or more electrodes in each. For example, the power source 252 can be operably connected to a switch or gate configured to close a circuit having the first and second electrodes 218 and 228 therein. In an embodiment, the power source 252 can include a micro-battery or any other battery having a suitably small enough size to be able to fit into the IOL system 200. Suitable batteries can include a thin film battery, a button cell battery, or any other miniaturized battery. A suitable thin film battery can include a flexible thin film lithium-ion battery, such as the LiTe*STAR™ thin-film rechargeable battery or Thinergy® battery by Infinite Power Solutions, or equivalents thereof. The battery can be configured to deliver 0.1 mV or more, such as about 0.1 mV to about 20 V, about 0.5 mV to about 5 V, about 0.5 V, about 1 V, about 2 V, or about 10 V or less. The battery can be configured to deliver 0.1 mA or more, such as about 0.1 mA to about 1 A, about 0.2 mA to about 0.5 mA, or about 1 A. In an embodiment, the time-averaged current drawn from the battery is dependent upon the frequency at which the lens makes focal length changes. The controller 250 can include a capacitor (not shown) operably coupled to the battery and configured to deliver a specific voltage such as any of those described above, or higher values by use of voltage boosting circuitry. Suitable capacitors can include thin film capacitors. The controller 250 can include voltage booster circuitry, configured to increase the voltage supplied by the battery to a higher voltage in order to increase the bias voltage applied to a capacitor or to the electrodes of the diffractive lens (and hence to the electric field acting on an electro-optically active material within the diffractive lens). The power source 252 may include a parasitic power device, such as an induction coil, thermoelectric device, or any other device configured to harvest energy from a subject. In an embodiment the power source 252 can include a sufficiently small thermoelectric device (e.g., thermoelectric generator) configured to charge a battery or capacitor via heat harvested through the thermoelectric device. In an embodiment, the power source 252 can include an induction coil configured to produce current from a changing magnetic field applied thereto. For example, the induction coil can include a channel having a magnet therein, the channel passing the induction coil upon movement of the subject (e.g., eye-movement or blinking). In an embodiment, an induction coil can be disposed in the eye of a subject (e.g., in or adjacent to the IOL) and a corresponding magnet may be positioned on an adjacent part of the subject (e.g., an eyelid or bridge of the nose) whereby movement of the eye or eyelid can cause a current in the induction coil. The power source 252 can include one or more photocells configured to harvest optical energy received either from ambient lighting or from an artificial or user-directed light source. The induction coil, photocell, or thermoelectric device can be configured to charge a battery or capacitor, and can be configured to utilize voltage booster electrical circuitry. The power source 252 can include any other suitably sized device capable of providing an electrical charge.

The control electrical circuitry 254 can be coupled to the power source 252 and optionally include one or more gates or switches configured to selectively permit the power source 252 to apply a bias to one or more electrodes coupled thereto. The gates or switches can include an RF switch or a microwave switch by way of example. The control electrical circuitry 254 can include an antenna (e.g., RF or microwave antenna) or another means of receiving a signal from an activation source, such as a remote control device (not shown) wirelessly coupled to the controller 250. Each of the one or more switches or gates can be configured to open or close only upon receipt of a specific stimulus, such as a specific radio frequency signal or a specific microwave frequency signal. In an embodiment, the controller 250 can include two separate circuits operably coupled to the power source 252 and the control electrical circuitry 254, wherein a first circuit includes a switch configured to be actuated upon receiving a first radio frequency and a second circuit is configured to be actuated upon receiving a different, second radio frequency. Upon receipt of the specific radio frequency a switch can open or close. In an embodiment, one or more gates or switches can be located between the power source 252 and the control electrical circuitry 254, between the power source 252 and the electrical leads 256, or between the control electrical circuitry 254 and electrical leads 256.

In an embodiment, one or more of the controller 250, the power source 252, the control electrical circuitry 254, any other component of the controller 250, or at least a portion of one or more of the electrical leads 256 can be at least partially embedded within the haptic of an IOL. In an embodiment, an IOL system can include an activation source (not shown) such as a RF or microwave signal generator configured to selectively provide an activation stimulus or signal effective to direct the controller 250 (or a component thereof) to apply a bias across one or more electrodes. In an embodiment, the controller 250 can include a sensor configured to automatically detect if a different focal length is needed and responsive thereto, automatically direct the control electrical circuitry 254 or power source 252 to apply an electrical bias to one or more electrodes operably couple therewith. Such sensors can include one or more magnetic sensors configured to sense the point of focus through the alignment of magnetic markers in each eye of subject, a sensor configured to determine alignment of the eyes via relationship to a reference point remote from the subject, a sensor to determine a force applied by the eye's ciliary muscle (e.g., to the IOL's haptic), a sensor to determine the range to an object being observed via the IOL, or the like.

In an embodiment, the IOL system 200 can include one or more sensors configured to detect one or more physiological indicia. For example, the IOL system can include one or more physiological sensors configured to detect a physiological parameter in the eye of a subject such as glucose concentration, eye (e.g., intraocular) pressure, heart rate, pulse, temperature, biological proteins present in the eye, or any other biological indicia. The one or more (e.g., physiological) sensors can be disposed within the IOL such as in the haptic of the IOL (FIG. 1A) or the diffractive lens. In such embodiments, the one or more physiological sensors can be hermetically sealed within the IOL or a packaging affixed thereto. In some embodiments, the one or more sensors can be disposed remotely from the IOL such as on a wearable device or remote sensor station (e.g., on a desk or wall). The one or more physiological sensors can include a glucose sensor, a heart rate sensor, a pulse oximeter, a temperature sensor, a moisture sensor, or another suitable physiological sensor. The physiological sensors can be configured to output one or more physiological signals responsive to sensing one or more physiological characteristics. For example, the physiological sensors can transmit (e.g., via a transmitter thereon (not shown)) the physiological signals to the controller 250 or to a device remote from the IOL. For example, the physiological sensor can transmit the physiological signals to an implanted or implantable device, a wearable device, or a computer or network that includes patient records. The one or more sensors can be operably coupled to the controller 250. The controller 250 of the IOL system 200 may be configured to transmit the measurements of the physical indicia to a remote source such as a computer, a cellular phone, or other electronic device. In some embodiments, the measured physical indicia may be used to determine the health of a subject or eye thereof (e.g., determine if a subject is suffering from glaucoma), customize the operation of the IOL to the particular subject, determine if the IOL needs to be removed or adjusted, or determine if the focal adjustments of the IOL are suitable for the subject. The electronic device may then transmit instructions to the controller 250 to selectively control or otherwise adjust the functioning of the IOL, responsive to the sensed physical indicia. While shown connected to the single diffractive lens 202, the controller 250 or second controller 250 can be operably coupled to at least one more diffractive lens in a similar or identical manner as disclosed above with reference to FIG. 7. In any event, the controller can be used to selectively change the focal length of the associated lens system to one or more alternative focal lengths. Any of the IOLs, diffractive lenses, or haptics herein can include a protective coating over at least a portion thereof sufficient to limit or prevent any materials or electrical bias from harming or unintentionally altering the surrounding tissue of the eye. Suitable protective coatings can include any of those materials known to be stable and inert when implanted in a subject such as a mammal (e.g., human).

The control electrical circuitry 254 can include a processor operably coupled to a memory storage medium (e.g., a hard drive). The processor can access and execute one or more machine readable operational programs stored in the memory storage medium. The processor can selectively control one or more electrodes to apply a selected bias to the diffractive lens, such as over a selected duration or increase or decrease the bias at a selected rate.

Figure 8A:
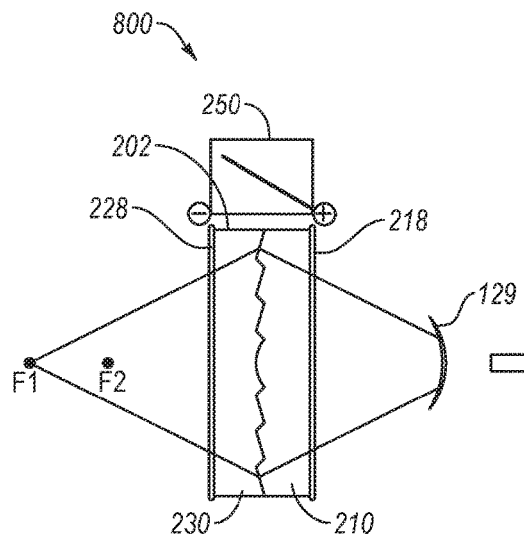
FIGS. 8A and 8B are schematic side, cross-sectional views of a portion of the diffractive lens of an IOL system before and after activation of the electro-optical material therein, according to an embodiment.
Figure 8B:
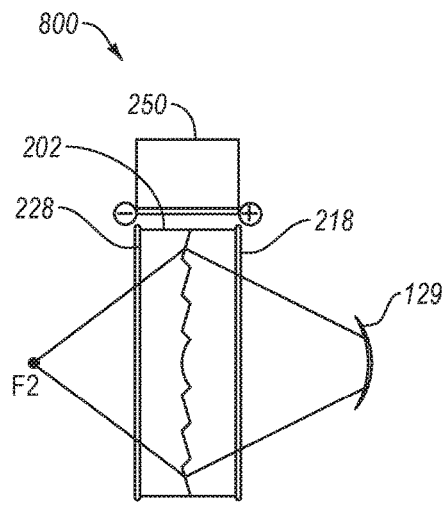

FIGS. 8A and 8B are schematic side, cross-sectional views of an IOL system 800 before and after a bias is applied between the electrodes therein, respectively, according to an embodiment. Methods of modifying a focal length of an IOL system can include providing an IOL system, such as any described IOL system or component herein, and biasing at least some of the electrodes therein to modify an index of refraction of one or more materials therebetween. The IOL system 800 can include one or more diffractive lenses, such as diffractive lens 202. The diffractive lens 202 can be configured similarly or identical to any diffractive lens herein, such as a diffractive lens including at least one material 210 or 220 therein having an electrically-modifiable index of refraction (e.g., electro-optical material), one or more electrodes 218 or 228, and a control system (not shown) configured to provide an electrical bias between the one or more electrodes 218 and 228. The at least one material 210 or 220 can be similar or identical to any of the first or second materials herein, including any surfaces, compositions, shapes, or other properties associated therewith. The one or more electrodes 218 or 228 can be similar or identical to any first or second electrode herein, including any surfaces, compositions, positions, shapes, or other properties associated therewith. The IOL system 800 can include a controller 250 similar or identical to any controller disclosed herein, including any components, circuits, or configurations thereof. The controller 250 can include a circuit including one or more of the power source, the control electrical circuitry, and the first and second electrodes 218 and 228.

In a ground or inactive state shown in FIG. 8A, the circuit can be open, such that no bias is applied between the electrodes 218 and 228. In the ground state, the IOL system 800 exhibits a first focal length F1. In the ground or inactive state, light passing through the diffractive lens 202 can be focused onto the retina 129 of a subject having the IOL system 800 implanted therein. In certain instances, a subject may not be able to focus at a second focal length F2 without assistance. In such instances, a bias can be selectively applied to the first and second electrodes 218 and 828, effective to modify the index of refraction of one or more electro-optical materials therebetween (e.g., the first material 210 or the second material 220). In an embodiment, a method of modifying a focal length of the IOL system 200 can include, via the controller 250, biasing the first and second electrodes to modify the index of refraction of one or more electro-optical materials therein. In an embodiment, a method of modifying a focal length of the IOL system 800 can include, via the controller 250, biasing the first and second electrodes to modify the index of refraction of a first electro-optical material and a second electro-optical material therein. In an embodiment, biasing the first and second electrodes 218 and 228 can include biasing the first and second electrodes 218 and 228 for a fixed amount of time. The fixed amount of time can be programmed into control electrical circuitry (or memory associated therewith) or be determined by the length of time that a stimulus is applied to the controller from an activation source (e.g., remote source of RF radiation). Suitable fixed times can include 30 seconds or more, such as 1 minute to 2 hours, 5 minutes to 1 hour, 10 minutes to 30 minutes, more than 10 minutes, less than 5 minutes, or more than 1 hour. In an embodiment, biasing the first and second electrodes 218 and 228 can include biasing the first and second electrodes 218 and 228 for an amount of time determined by the time for which the modified focal length is desired.

As shown in FIG. 8B, upon activation of the controller 250, the circuit including the controller 250 and the first and second electrodes 218 and 228 is closed thereby biasing the first and second electrodes 218 and 228 and the material therebetween. Upon biasing the first and second electrodes 218 and 228, the index of refraction of at least the electro-optical material in the first material 210 can be electrically modified to induce a modified index of refraction and the IOL system 800 can exhibit the second focal length F2. In an embodiment, the diffractive lens 202 can be configured such that the first focal length F1 can be greater than the second focal length F2. In an embodiment, the diffractive lens 202 can be configured such that the second focal length F2 can be greater than the first focal length F1. In an embodiment, a refractive lens can be used optically in series with the diffractive lens 202, similar or identical to that shown in FIG. 3. In an embodiment, an IOL system can include at least one additional diffractive lens in series with the first diffractive lens similar or identical to those shown in FIGS. 4 and 5. In such embodiments, more than 2 focal lengths can be obtained by selectively applying a bias to one or more electrodes associated therewith.

Figure 9:
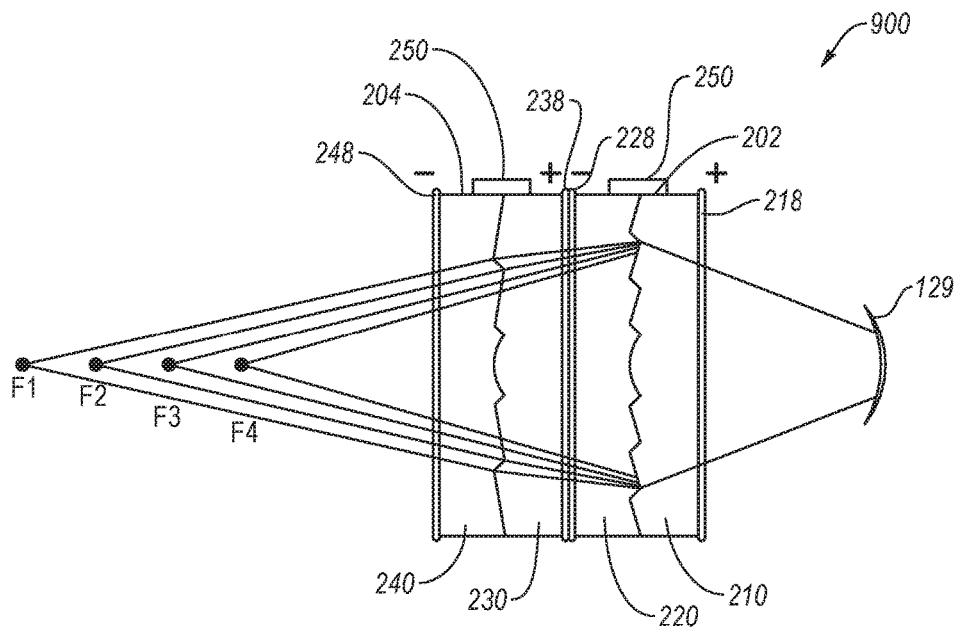
FIG. 9 is a schematic side, cross-sectional view of a portion of the diffractive lens of an IOL system having multiple focal lengths according to an embodiment.

FIG. 9 is a schematic side, cross-sectional view of an IOL system 900, according to an embodiment. The IOL system 900 can include more than one diffractive lens therein. The IOL system 900, or portions thereof, can be configured similarly or identical to the IOL systems shown in FIGS. 4 and 5. For example the IOL system 900 can include a first diffractive lens 202 and a second diffractive lens 204. The first diffractive lens 202 and a second diffractive lens 204 can be similar or identical to those diffractive lenses 202 and 204 described with respect to FIGS. 4 and 5, including any portions of components thereof. For example, the first diffractive lens 202 can include the first material 210 and the second material 220, and the second diffractive lens 204 can include the third material 230 and the fourth material 240, as described above. The IOL system 900 can include a plurality of electrodes 218-248. For example, the first electrode 218 can be disposed adjacent to the first material 210, the second electrode 228 can be positioned adjacent to the second material 220, the third electrode 238 can be positioned adjacent to the third material 230 or the fourth material 240, and the fourth electrode 248 can be positioned adjacent to the fourth material 240. The electrodes 218, 228, 238 and 248 can be similar or identical to those described above with reference to FIGS. 4 and 5. The IOL system 900 can include one or more controllers 250 operably coupled to one or more of the electrodes 218-248. The one or more controllers 250 can be configured or positioned in any manner disclosed herein, such as those described above with reference to FIGS. 4 and 5.

In an embodiment, none of the diffractive lenses 202 or 204; the first diffractive lens 202; the second diffractive lens 204; or both diffractive lenses 202 and 204 can be selectively biased, thereby altering the index of refraction of one or more electro-optical materials therein and the focal length of the IOL system 900. The IOL system 900 having the first diffractive lens 202 and the second diffractive lens 204 can include four selectively controllable focal lengths. For example, the first diffractive lens 202 can include one or more materials having an electrically-modifiable index of refraction and the second diffractive lens 204 can include one or more materials having an electrically-modifiable index of refraction. The electrodes 218-248 individually associated therewith can be selectively biased to alter only one of, or both of, the indices of refraction of the electro-optical materials in the first diffractive lens 202 or the second diffractive lens 204. In a ground or inactive state, the IOL system 900 can exhibit a first focal length F1. In an embodiment, the first and second electrodes 218 and 228 can be biased to modify the index of refraction of one or both of the first or second materials 210 or 220 in the diffractive lens 202. Upon application of the bias to the first and second electrodes 218 and 228 by the controller 250, the index of refraction of at least one of the electro-optical materials in the first diffractive lens (e.g., first material 210 or second material 220) can be modified and the IOL system 900 can exhibit a second focal length F2.

In an embodiment, the IOL system 900 can include the second diffractive lens 204 having the third and fourth electrodes 238 and 248 disposed adjacent to the third and fourth materials 230 and 240 respectively, as shown in FIG. 9. In an embodiment, modifying the focal length of the IOL system 900 can include selectively biasing the third and fourth electrodes 238 and 248 to change the index of refraction of one or both of the third or fourth materials 230 and 240. Upon application of the bias to third and fourth electrodes 238 and 248 by the controller 250, the index of refraction of one or more electro-optical materials in the second diffractive lens 204 can be modified and the IOL system 900 can exhibit a third focal length F3. In an embodiment, modifying the focal length of the IOL system 900 can include selectively biasing one or both of the first and second electrodes 218 and 228 or the third and fourth electrodes 238 and 248 to change the index of refraction of one or more of the first, second, third, or fourth materials 210-240, respectively associated therewith. In an embodiment, modifying the focal length of the IOL system 900 can include selectively biasing one of the first and second electrodes 218 and 228, or the third and fourth electrodes 238 and 248, at a time. In an embodiment, modifying the focal length of the IOL system 900 can include selectively biasing both of first and second electrodes 218 and 228 and the third and fourth electrodes 238 and 248 substantially simultaneously. In an embodiment, modifying the focal length of an IOL can include providing an activation signal to the controller 250, such as from an activation source (e.g., remote RF signal generator). The activation signal can include instructions effective to bias one or more of the first and second electrodes 218 and 228; or the third and fourth electrodes 238 and 248.

In an embodiment, modifying the focal length of an IOL can include biasing all of the electrodes 218-248, wherein the electrically-modifiable index of refraction of one or more materials 210-240 in each of the first diffractive lens 202 and the second diffractive lens 204 can be modified to alter the focal length of the IOL system 900 to provide a fourth focal length F4. The controller 250 can be configured to selectively bias one or more of the electrodes 218-248. In an embodiment, a refractive lens can be placed in series with the diffractive lenses 202 and 204, such as described above with reference to FIG. 5.

In an embodiment, the IOL system 900 can include the second diffractive lens 204 having the third electrode 238 disposed adjacent to one of the third or fourth materials 230 or 240 and the opposite side of the diffractive lens 204 can be placed adjacent to the first electrode 218 or the second electrode 228, substantially as shown in and described with respect to FIG. 4. In an embodiment of a method of modifying the focal length of the IOL system 900, the third electrode 238 and one of the first or second electrodes 218 or 228 can be selectively biased using the controller 250 to selectively change the index of refraction of one or both of the third or fourth materials 230 and 240. Upon application of a bias to the third electrode 238 and one of the first or second electrodes 218 or 228 by the controller 250, the index of refraction of one of the electro-optical materials in the second diffractive lens 204 can be modified and the IOL system 900 can exhibit the third focal length F3.

In an embodiment, modifying the focal length of an IOL can include biasing all of the electrodes 218-238, wherein the electrically-modifiable index of refraction of one or more materials 210-240 in each of the first diffractive lens 202 and the second diffractive lens 204 can be modified to alter the focal length of the IOL system 900 to provide the fourth focal length F4. The controller 250 can be configured to selectively bias one or more of the electrodes 218-238. The shared electrode 218 or 228 between the first diffractive lens 202 and the second diffractive lens 204 can be operably connected to two circuits having separately controlled gates or switches capable of selectively providing a bias to only a single set of electrodes at a time or both sets of electrodes substantially simultaneously. In an embodiment, a refractive lens can be placed in series with the diffractive lenses 202 and 204, such as described above with reference to FIG. 5.

In an embodiment, the first focal length F1 associated with the inactive state of the first and second diffractive lenses 202 and 204 (e.g., unbiased electrodes corresponding to unaltered indices of refraction in the materials therein) can be greater than one or more of the second focal length F2, the third focal length F3, or the fourth focal length F4.

In an embodiment, the second focal length F2 associated with the active state of the first diffractive lens 202 can be greater than the third focal length F3 or the fourth focal length F4. (e.g., electrically biased state of the electro-optical material inducing an electrically-modified index of refraction in one or more of the first or second materials 210 or 220)

In an embodiment, the third focal length F3 associated with the active state of the second diffractive lens 204 can be greater than the fourth focal length F4. In an embodiment, the third focal length F3 can be greater than the second focal length F2. In an embodiment, the method of modifying the focal length of an IOL can include, via the controller 250, biasing the third electrode 238 and the fourth electrode 248 to modify at least the electrically-modifiable third index of refraction of the third material 230 and the focal length of the IOL system 900 to achieve the third focal length F3.

In an embodiment, the method of modifying the focal length of an IOL further includes, via the controller 250, biasing the third electrode 238 and the one of the first or second electrodes 218 or 228 to modify at least the electrically-modifiable third index of refraction of the third material 230 and the focal length of the IOL system 900 to achieve the third focal length F3. In an embodiment, biasing the third electrode 238 and the one of the first or second electrodes 218 or 228 can include selectively biasing only one of: the first and second electrodes 218 and 228; or the third electrode 238 and the one of the first or second electrodes 218 or 228, at a time. In an embodiment, biasing the third electrode 238 and the one of the first or second electrodes 218 or 228 can include selectively biasing both of the first and second electrodes 218 and 228; and the third electrode 238 and the one of the first or second electrodes 218 or 228, substantially simultaneously. In an embodiment, modifying the focal length of an IOL can include providing an activation signal to the controller 250, such as from an activation source. The activation signal can include instructions effective to or cause the controller 250 to bias one or more of the first and second electrodes 218 and 228; or the third and electrode 238 and one of the first electrode 218 or the second electrode 228.

In an embodiment, the fourth focal length F4 associated with the active state for both the first and second diffractive lenses 202 and 204 can be less than one or more of the first focal length F1, the second focal length F2, or the third focal length F3.

In an embodiment, modifying the focal length of an IOL can include determining a selected focal length. Determining a selected focal length can include determining a selected focal length based on an activity such as reading, watching television or a live performance, playing a sport, or any other activity. A selected focal length can be programmed into the controller 250 corresponding to a specific activity and can be selectively induced by biasing one or more electrodes in an IOL based on participation in the activity. In an embodiment, biasing the one or more of the first and second electrodes 218 and 228 or the third and fourth electrodes 238 and 248 to modify at least the electrically-modifiable first index of refraction of one or more of the first, second, third, or fourth materials 210-240 and a focal length of the intraocular lens system 900 includes selectively biasing one or more of the first and second electrodes 218 or 228 or the third and fourth electrodes 238 or 248 responsive to the selected focal length.

In an embodiment, modifying the focal length of an IOL can include providing an IOL having at least one electro-optical material having a plurality of tunable focal lengths (e.g., collectively forming a gradient), each focal length being dependent upon the amount of voltage applied to the electro-optical material. For example, an IOL having a plurality of tunable focal lengths can include a first, electro-optical material having a Fresnel lens configuration, and a second, electro-optical or inert material having a complementary geometry to the first electro-optical material. The Fresnel lens blazing can be configured to focus one or more of a plurality of orders of light onto the retina of a subject, each order being induced by a change in the refractive properties of the first electro-optical material due to a specific electrical bias. Each individual order of light of the plurality of orders of light can be focused by inducing a specific voltage at the electro-optical material(s). The individual orders of light can be gradually changed from one to another, thereby allowing a tunable gradient of focal lengths. In an embodiment, the second material can be configured as a Fresnel lens, and the first material can exhibit complementary surface geometry to the second material such that an interface between the two materials is substantially seamless. In such an embodiment, the first material may be inert or an electro-optical material and the second material may be an electro-optical material the same as or different than the first electro-optical material. The IOL systems having the tunable focal length as described above may be substantially similar to or identical to any IOL system disclosed herein, including one or more components thereof.

Modifying the focal length of the IOL having a plurality of tunable focal lengths can include gradually adjusting the electrical bias to the first and second electrodes until a desired focal length is reached. The desired focal length can be between a maximum focal length of the inactive IOL and the minimum focal length of the fully biased IOL (e.g., biased to the fullest extent of the power source or materials therein). Gradually adjusting the electrical bias can include gradually increasing or decreasing the electrical bias to gradually increase or decrease the focal length of the IOL.

In an embodiment, modifying the focal length of an IOL can include providing an IOL, such as any IOL described herein. In an embodiment, modifying the focal length of an IOL can include positioning an IOL within the eye of a subject. Positioning an IOL within the eye of a subject can include surgically implanting an IOL in the eye of a subject.

In some embodiments, modifying the focal length(s) of an IOL can include modifying an effective focal length from a first effective focal length to one or more additional effective focal lengths over a selected duration of time. The controllers disclosed herein can be configured (e.g., have machine readable programs) to selectively control application of an electrical bias to the electrodes effective to control the transition from the first effective focal length to one or more additional effective focal lengths in a time dependent manner, such as slower than a duration that an average human eye requires to accommodate between different focal lengths. The selected duration of time over which the bias is selectively transitioned from a first bias to one or more additional biases can be selected to provide a transition from a corresponding first effective focal length to a corresponding one of the one or more additional focal lengths. In such a manner, it is possible to provide a smooth or stepped transition in human perceived effective focal lengths using IOLs.

Figure 10:
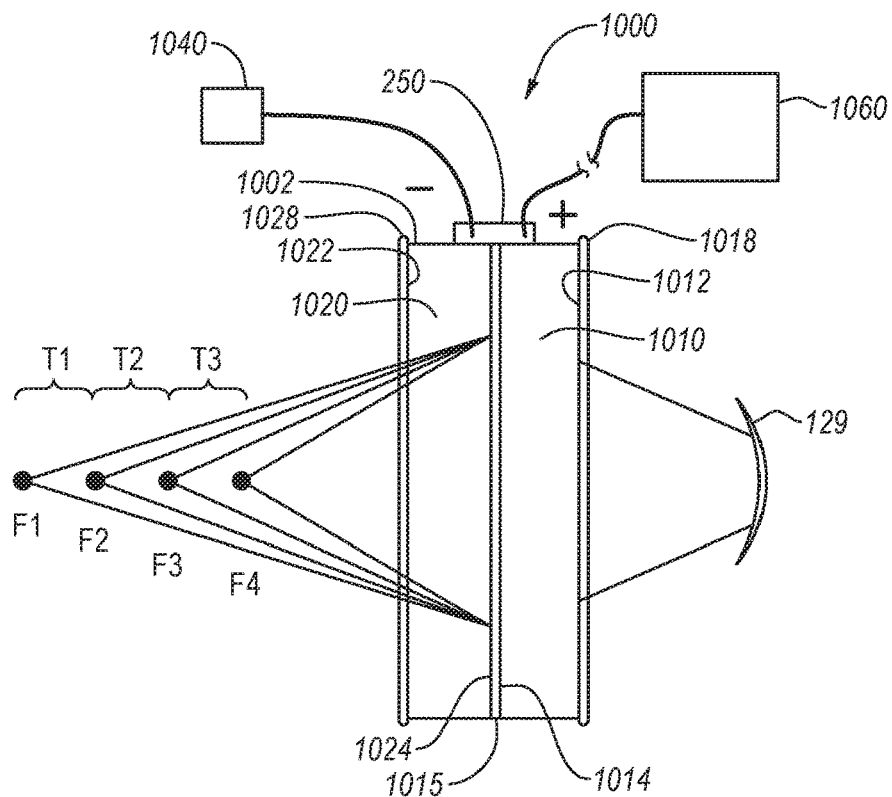
FIG. 10 is a schematic of an IOL system including a side cross-sectional view of a portion of a diffractive lens according to an embodiment.

FIG. 10 is a schematic of an IOL system 1000 including a side cross-sectional view of a portion of a diffractive lens 1002 according to an embodiment. The IOL system 1000 includes the diffractive lens 1002 and a controller 250. The diffractive lens 1002 can be sized, shaped, and composed of materials suitable to be implanted in an eye of a subject (e.g., human being or other animal). In some embodiments, the IOL system 1000 can include a user interface 1060 operably coupled to the controller 250. The IOL system 1000 can be configured to selectively modify an effective focal length from a first effective focal length to at least a second effective focal length over a selected duration of time. Such selective modification can be carried out by selectively applying one or more electrical biases to one or more electrodes positioned adjacent to one or more materials in the diffractive lens 1002 having an electrically-modifiable index of refraction over the selected duration of time. The applied electrical biases can modify an index of refraction and a corresponding diffraction pattern of the one or more materials in the diffractive lens 1002, over the selected duration of time. For example, an applied first electrical bias can be changed (e.g., transitioned or stepped) to at least a second electrical bias over a selected duration of time that is greater than the duration of time required for an average human eye to accommodate a change in focal lengths (e.g., more than about 350 ms). Accordingly, the IOL system 1000 can provide a selectively controllable (e.g., perceived smooth) transition between the first effective focal length and the at least a second effective focal length to the user of the IOL system 1000. In some embodiments, the applied first electrical bias can be changed to at least the second electrical bias over a selected duration of time that is less than the duration of time required for an average human eye to accommodate a change in focal lengths, such as less than about 350 ms. In some embodiments, the applied first electrical bias (e.g., bias state) can include no applied electrical bias, whereby the at least a second electrical bias includes the first instance of application of actual electrical energy the first and/or second electrodes 1018 or 1028.

The diffractive lens 1002 can be similar or identical to any of the diffractive lenses disclosed herein in one or more aspects, such as diffractive lens 202 or 602 described herein. The diffractive lens 1002 can include a first material 1010 and a second material 1020. The first material 1010 and second material 1020 can be similar or identical to any of the first and second materials disclosed herein in one or more aspects such as material species, dimension(s), or configuration with respect to adjacent material(s). In some embodiments, one or more of the first material 1010 or the second material 1020 can have an electrically-modifiable index of refraction. In some embodiments, the first material 1010 and the second material 1020 can have substantially the same DC dielectric constant. In some embodiments, one or more of the first material 1010 or the second material 1020 can include an electro-optical material, such as at least one of lithium niobate, lithium tantalate, lead zirconate titanate, potassium dihydrogen phosphate, or cadmium telluride. In some embodiments, one or more of the first material 1010 or the second material 1020 can include a solid state electro-optical material or a liquid crystal The first material 1010 can include a first outer surface 1012 and the second material 1020 can include a second outer surface 1022 on the generally opposite side of the diffractive lens 1002 than the first surface 1012. The first material 1010 and the second material 1020 can include an interface 1015 therebetween (shown in FIG. 10 as a block). The interface 1015 (shown as a block) can include a respective interfacial surface of each of the first material 1010 and the second material 1020. For example, the first material

1010 can include a first interfacial surface 1014 and the second material 1020 can include a second interfacial surface 1024. While illustrated in FIG. 10 as a block, in some embodiments, the first and second interfacial surfaces 1014 and 1024 can be configured similarly or identical to the first and second diffraction surfaces 214 and 224 (FIG. 2). In some embodiments, the at least one of interfacial surfaces 1014 and 1024 can include an electrically-modifiable diffraction pattern therein. For example, each of the first and second interfacial surfaces 1014 and 1024 can be diffraction surfaces, where the first material 1010 includes a first index of refraction and/or first diffraction pattern and the second material 1020 includes a second index of refraction and/or a second diffraction pattern therein. In such embodiments, one or both of the first material 1010 and the second material 1020 can include an electrically-modifiable diffraction pattern. The electrically-modifiable diffraction pattern can be electrically-modifiable via a change in diffraction of the first material 1010 (e.g., at least partially due to a change in the electrically-modifiable index of refraction thereof), a change in diffraction of the second material 1020 (e.g., at least partially due to a change in the electrically-modifiable index of refraction thereof), or an electrically-modifiable coating on one or more of the first material 1010 or the second material 1020. During the change in the diffraction pattern (as induced by the change in the index of refraction), the effective focal length can be correspondingly changed (e.g., increased or decreased) based on the amount (e.g., light fraction) and focal point of the light delivered therefrom.

The IOL system 1000 can include a first electrode 1018 disposed adjacent to the first material 1010 and at least a second electrode 1028 can be adjacent to the second material 1020. For example, the first electrode 1018 can be adjacent to the first outer surface 1012 of the first material 1010 and the second electrode 1028 can be adjacent to the second outer surface 1022. The first and second electrodes 1018 and 1028 can be similar or identical to any of the electrodes disclosed herein, in one or more aspects. For example, the first and second electrodes 1018 and 1028 can be substantially transparent to visible light or can include any of the electrode materials disclosed herein (e.g., a transparent conductive polymer). The first and second electrodes 1018 and 1028 can be operably coupled to one or more of a power supply (not shown) or a controller 250 configured to selectively control the application of electrical bias thereto. The first electrode 1018 and the second electrode 1028 can extend over a portion of, or an entire area of, the first outer surface 1012 and the second outer surface 1022, respectively.

The controller 250 can be configured to selectively control application of electrical bias to one or more of the first electrode 1018 and the at least a second electrode 1028 over a selected duration of time. More specifically, the controller 250 can be configured to selectively control the selected duration of time over which a transition from a first bias state (e.g., a first voltage) to at least a second bias state occurs. In some embodiments, the controller 250 can include at least one selected duration of time stored in the memory storage medium of the control electrical circuitry 254 (FIG. 7). The at least one selected duration of time can include one or more selected durations of time set by a manufacturer, which may correspond to an age of a user, a physiological condition of a user (e.g., astigmatism, near-sightedness, glaucoma, etc.), or a distance between the effective focal lengths (or intermediate focal length(s) therebetween). The at least one selected duration of time can include one or more selected durations of time set by a user, a device technician, or a medical professional, which may correspond to an age of a user, a physiological condition of a user, a distance between the effective focal lengths, or a selected duration of time based on personal preference of the user. The at least one selected duration of time can include one or more selected durations of time automatically set by the controller 250 responsive to sensed feedback from one or more sensors, a time of day, a sensed distance between objects (e.g., and the effective focal lengths therebetween). Each of the one or more selected durations of time can be associated with a specific amount or rate of change of an electrical bias (e.g., the controller can direct the electrodes to apply a specific change in bias over a selected duration of time) selected from a plurality of electrical biases stored in the memory storage medium. For example, transition from a first effective focal length to a second effective focal length can be carried out over a selected duration of time by the controller via association of the selected duration of time with a selected change in bias states from a first bias state (e.g., a first amount of bias) to a second bias state (e.g., second amount of bias) over the selected duration of time.

The processor of the controller 250 can be configured to access and execute application of an electrical bias of any one or more selected durations of time stored in the memory storage medium, effective to provide a selected transition from one effective focal length to at least a second effective focal length. The controller 250 (e.g., processor therein) can be operably coupled to a power source or supply and/or one or more electrodes and can be configured to selectively bias the one or more electrodes according to the duration of time. For example, the controller 250 can selectively bias one or more of the first and second electrodes 1018 or 1028 effective to modify at least the electrically-modifiable index of refraction, the electrically-modifiable diffraction pattern, and an effective focal length of the intraocular lens system 1000 from a first effective focal length to at least a second effective focal length over the selected duration of time (e.g., such as via one or more intermediate focal lengths therebetween). The power source can be operably coupled to the electrodes or any other portion of the IOL system 1000.

For example, as shown in FIG. 10, ground or inactive state, light passing through the diffractive lens 1002 can be focused onto the retina 129 of a subject having the IOL system 1000 implanted therein. In certain instances, a subject may not be able to focus on at least a second focal length (e.g., F2, F3, or F4) without assistance or may experience discomfort due to rapid leaps (e.g., faster than an eye can accommodate to) in effective focal length of the IOL during a transition between one or more focal lengths. Accordingly, the IOL system 1000 can be configured to cause a transition from the first effective focal length F1 to at least a second effective focal length (e.g., second effective focal length F2, third effective focal length F3, and/or fourth effective focal length F4), at a specific rate or via a specific number of intermediate focal lengths.

In some embodiments, the first effective focal length F1 can be achieved while the IOL system 1000 is in a first bias state (e.g., a first bias or no bias is applied). Upon activation, the IOL system 1000 can change the effective focal length to one or more additional effective focal lengths, depending on the distance between the objects/focal lengths. For example, the IOL system 1000 can change (e.g., bias the diffractive lens to change an index of refraction and thereby the diffraction pattern and thereby the effective focal length) from the first effective focal length F1 to the second effective focal length F2 over a selected first duration of time T1. The selected first duration of time T1 can be at least about 350 ms, such as about 350 ms to about 2 s, about 400 ms to about 1 s, about 450 ms to about 750 ms, about 500 ms to about 1 s, about 750 ms to about 1.5 s, about 350 ms to about 500 ms, about 500 ms to about 750 ms, greater than about 400 ms, or greater than about 500 ms. In such embodiments, the selected first duration of time T1 can be greater than the duration of time that it takes an average human (or other animal) eye to accommodate between focal points, such that a substantially smooth transition between focal points/lengths is perceived. In some embodiments, the selected first duration of time T1 can be less than about 350 ms, such as about 100 ms to about 350 ms, about 150 ms to about 300 ms, about 200 ms to about 350 ms, or less than about 200 ms. The selected duration of time T1 can be selected based upon the transition of the effective focal length from near to far or far to near; the distance the focal lengths are from the subject; the age of the subject, the physiological condition of the eyes of the subject, etc.

In some embodiments, the controller 250 can control application of electrical bias(es) effective to produce a series of transitions between multiple effective focal lengths. For example, the controller 250 can (including programming stored therein to) apply at least one intermediate bias between the first bias state (corresponding to the first effective focal length) and a second bias state (corresponding to the first effective focal length). The at least one intermediate bias can include a plurality of intermediate bias states each of which includes an incrementally increasing (or decreasing) effective focal length approaching the second effective focal length, wherein the second effective focal length is longer (or shorter) than the first effective focal length. The controller 250 can (including programming stored therein to) incrementally increase or decrease the bias applied to the first and second electrodes 1018 and 1028 by one or more distinct amounts (e.g., of voltage) effective to induce one or more distinct intermediate focal lengths (e.g., F2 and/or F3) between the first effective focal length F1 and the at least a second effective focal length (e.g., F4). For example, the IOL system 1000 can change from the first effective focal length F1 to the fourth effective focal length F4 via the second and third effective focal lengths F2 and F3 over three selected durations of time T1, T2, and T3. The selected durations of time T1, T2, and T3 can be respectively disposed between the focal lengths F1-F4. Each selected duration of time T1, T2, and T3 can be identical, or each can differ from one or more of the other selected durations of time T1, T2, and T3. The selected durations of time T1, T2, and T3 can include any of the durations of time disclosed above for T1. The selected durations of time can differ depending on the transition from near to far or far to near; the distance the focal lengths are from the subject; the age of the subject, the physiological condition of the eyes of the subject, etc. In some embodiments, more or fewer durations can be used than 3.

In some embodiments, the first effective focal length F1 can be achieved at a first bias state (e.g., first bias or no bias). Upon a selected change in focus of the subject, the controller 250 can control application of bias to the electrodes to induce a change from the first bias state and the corresponding first effective focal length F1 to the second bias state (e.g., first or second applied bias) and the corresponding second effective focal length F2 over the first selected duration of time T1. The controller 250 can selectively control further application of bias to the electrodes to induce a change from the second bias state and the corresponding second effective focal length F2 to the third bias state (e.g., second or third applied bias) and the corresponding third effective focal length F3 over the second selected duration of time T2. The controller 250 can selectively control further application of bias to the electrodes to induce a change from the third bias state and the corresponding third effective focal length F3 to the fourth bias state (e.g., third or fourth applied bias) and the corresponding fourth effective focal length F4 over the third selected duration of time T3. The retina 129 can perceive a smooth transition between the effective focal lengths F1-F4 corresponding to the selected durations of time T1-T3. Fewer or greater numbers of transition states, selected durations of time, and/or effective lengths are considered herein, such as at least about 2, 3, 4, 5, or 10 transitions between an initial effective focal length and a final effective focal length.

Each of the selected durations of time T1, T2, and T3 can be immediately applied after termination of a previous selected duration, or can be separated by a dwell time at a specific effective focal length therebetween. For example, a dwell time at the second effective focal length F2 can be held by the controller 250 prior to transitioning the second bias state to the third bias state over the second selected duration of time T2. In such embodiments, the dwell times may allow a subject's eye to accommodate between differing effective focal lengths effective to provide a perceived smooth transition between focal lengths. Dwell times can include any of the selected durations disclosed above for the first selected duration of time T1.

The controller 250 can selectively adjust the selected duration(s) of time responsive to manual input by a user or automatically responsive to one or more of an age of a user of the intraocular lens system, a sensed distance between a first focal point and a second focal point, a time of day, a sensed intensity of light in a location of the user, or a sensed color of light in the location of the user. For example, the processor can access a look-up table having a plurality of discrete durations of time and electrical biases stored on the memory storage medium and corresponding to an average time of which the eye of a user of a selected age (e.g., average human of the same age) requires to accommodate from the first focal length to the second focal length. Based thereon, the processor can cause the electrodes to change from the first bias state to the second bias state over the selected duration corresponding to the age of the user as found in the look-up table. The processor can correlate one or more criteria, such as age of the user with the distance between the first focal point (e.g., first object) and second focal point (e.g., second object), and automatically select the selected duration of time based on the one or more criteria.

As depicted in FIG. 10, the user interface 1060 can be operably coupled to the controller 250. The user interface 1060 can include one or more of a keyboard, a visual display, a monitor, a keypad, at least one dial, a touchpad, a smartphone having a corresponding application (e.g., user interface application) stored thereon, at least one computer communication port, a button, or a switch. The user interface 1060 can be operably coupled to the controller via one or more of a wireless connection or a hardwired connection. The user interface can be located with or proximate to the user or can be remote from the user. The user interface 1060 can allow input into the controller 250 (e.g., into the memory or processor thereof) by one or more of a user (e.g., subject) of the intraocular lens system, a medical professional, a manufacturer, or a computing device. The input can include one or more of a selected duration of time, an activation command, a deactivation command, a command to apply a specific amount of bias to one or more of the first or second electrodes, a command to apply a specific amount of bias at a specific rate or specific intervals (e.g., transition from one bias to another over a selected duration of time), a machine readable program including any of the foregoing, or adjustments to any of the foregoing. For example, a user can input a selected duration of time into the user interface 1060 (and associated controller 250) and/or associate a selected duration of time with a specific focal length. The user can associate a selected duration of time with a specific focal length by entering into the memory storage medium, via the user interface 1060, that if a specific focal length is required, a transition thereto should be carried out over a specific selected duration of time. In such a manner, a user of the intraocular lens system 1000, a medical professional, a manufacturer, or a computing device can customize the use of the IOL system 1000 to the user's needs or preferences.

The effective focal lengths can include a combination of fractional percentages of light delivered from different (e.g., discrete) diffractive orders and associated discrete focal lengths. Put another way, the diffractive lens 1002 diffracts light into a set of discrete diffractive orders, wherein each electrical bias state defines a fractional delivery profile of light into each discrete diffractive order of the set of diffractive orders (and corresponding effective focal lengths). Each discrete diffractive order is associated with a discrete focal length. The first effective focal length can include or be associated with a set of discrete focal lengths defined by a first fractional delivery profile of light into the set of discrete diffractive orders. For example, the first effective focal length can include or be associated with delivery of a greater amount of light into a first discrete focal length than into any other of the set of discrete focal lengths. At least a second effective focal length can include or be associated with at least a second set of discrete focal lengths defined by at least a second fractional delivery profile of light into discrete diffractive orders. Accordingly, the at least a second effective focal length can include or be associated with delivery of a greater amount of light into at least a second discrete focal length than into any other of the set of discrete focal lengths. A change in electrical bias can provide or can be associated with a change in the fractional delivery of light into the set of discrete diffractive orders, and a corresponding change in fractional delivery of light into the set of discrete focal lengths.

The fractional percentages of light from two or more discrete diffractive orders (and associated discrete focal lengths) can combine to define an effective focal length. For example, a fourth effective focal length can be produced by a specific bias state thereby delivering about 40% of light to a third discrete focal length (via an associated discrete third diffractive order) and about 60% of light to a fourth discrete focal length (via an associated discrete fourth diffractive order) to form the fourth effective focal length-being a combination of the two discrete focal lengths. In some embodiments, a first percentage of light in an effective focal length can be provided from a first diffractive order and at least a second percentage of light can be provided from at least a second diffractive order. The percentages of light in an effective focal length from any one of the diffractive orders can be 10%, 20,%, 30, %, 40,%, 50%, 600/%, 70%, 800%, 90%, or ranges including any two of the foregoing as endpoints, and the remaining diffractive order(s) can constitute a remainder of the percentage of light.

The fractional percentages of light of a specific effective focal length can vary according to the refractive properties of the material(s) of the diffractive lens, the diffractive properties of the material(s) of the diffractive lens, and the amount of bias applied thereto. The individual or collective refractive and diffractive properties of the materials of the diffractive lens can be collectively altered by application of bias to one or more of the first electrode 1018 or the second electrode 1028. For example, in some embodiments, the first material 1010 can include an electro-optical material having a first electrically-modifiable index of refraction and the second material 1020 can include a second electro-optical material having a second electrically-modifiable index of refraction. Application of an electrical bias by one or more of the first or second electrodes 1018 or 1028 in adjacent to (e.g., in contact with) the first and second materials 1010 and 1020 can produce a change in the first and/or second electrically-modifiable index of refraction and by extension the diffraction pattern produced by the material(s). Accordingly, the effective focal length of the diffractive lens 1002 can be selectively altered. Moreover, the presence and/or amount of bias applied to one or more of the first and second materials can control the amount of change in the focal length of the diffractive lens 1002. Such amount can be selectively controlled in addition to the duration of time over which the transition from one bias state to another bias state is carried out. One or more intermediate focal lengths can be selected (e.g., by the controller) to be reached during a transition of bias and effective focal length. For example, the controller 250 can selectively bias the first electrode 1018 and the second electrode 1028 independently, effective to induce one or more intermediate focal lengths between the first effective focal length and the second effective focal length, from a collective refraction and diffraction of the first and second materials.

The intermediate focal lengths can each correspond to an intermediate bias state associated with a discrete bias between the first bias state (e.g., the first effective focal length) and at least the second bias state (e.g., the at least a second effective focal length). The controller 250 can apply at least one intermediate bias between a first bias state and at least a second bias state, independently, to each of the first electrode 1018 and the second electrode 1028 to provide a collective (and electrically-modifiable) index of refraction and diffraction of the first and second materials. In such embodiments, the first bias state of each of the first material and the second material can correspond to the first effective focal length. The second bias state of each of the first material and the second material can correspond to the second effective focal length. The at least one intermediate bias state or bias applied to one or more of the first material and the second material can correspond to the least one intermediate focal length, such as between the first and second effective focal lengths.

The controller 250 (e.g., processor of the control electrical circuitry 254) can execute one or more machine readable operational programs as stored in the memory storage medium, including one or more selected bias states and one or more selected durations of time. The machine readable operational programs can include selected durations of time, electrical bias amounts, one or more look-up tables providing values for correlating the electrical bias amounts to the selected durations of time, one or more preferred settings entered via the user interface, etc. The machine readable programs can include instructions for selectively biasing one or more of the first and second electrodes effective to modify at least the electrically-modifiable index of refraction and the effective focal length of the intraocular lens system from the first effective focal length to the second effective focal length over the selected duration of time.

In some embodiments, the system 1000 can include one or more sensors 1040 operably coupled to the controller (e.g., the memory storage medium or processor therein). The one or more sensors 1040 can include any of the sensors disclosed herein (e.g., physiological sensors). The one or more sensors 1040 can be positioned and be of the type to detect one or more of a distance between a first focal point and a second focal point (e.g., objects corresponding thereto), a time of day, an intensity of light in a location of a user of the intraocular lens system, or a color of light in the location of the user, a glucose concentration, heart rate, pulse, internal temperature of the subject, external temperature, moisture in a body part such as the eye, or any other characteristic. For example, the at least one sensor 1040 can include a glucose sensor, a heart rate sensor, a pulse oximeter, a temperature sensor, a moisture sensor, or another suitable physiological sensor. The at least one sensor 1040 can include a distance sensor (e.g., capacitive, photoelectric, or ultrasonic sensor), a light sensor (e.g., a photo cell, a photoresistor, a photodetector, a light emitting diode, etc.), a timer, or any other suitable sensor. The at least one sensor 1040 can be disposed on or in the diffractive lens 1002 such as on a surface of or embedded in the diffractive lens 1002 or a haptic thereof. The at least one sensor 1040 can be located remotely from the diffractive lens 1002, such as on a wearable device (e.g., armband, electrode, watch, etc.) or an object remote from the user (e.g., a sensor base located in an environment of the user, such as on a wall or table). The at least one sensor can be operably coupled to the controller via one or more of a wireless connection (e.g., when the sensors are remote from the diffractive lens and/or controller) or a hardwired connection (e.g., when integrated into or onto the diffractive lens). While shown as located on the diffractive lens 1002, in some embodiments, the controller can be located remote from the diffractive lens 1002, such as on a base in the environment of the user.

The controller 250 can include one or more machine readable programs therein configured to selectively adjust the selected duration of time and/or bias amount(s) responsive to one or more of an age of a user of the intraocular lens system, a sensed distance between the first focal point and the second focal point, a time of day, a sensed intensity of light in the location of the user, a sensed color of light in the location of the user, or any physiological condition of the user (e.g., subject wearing the IOL). For example, the controller can include programming configured to selectively adjust a number of one or more intermediate focal lengths induced by the bias(es) applied to the first and second electrodes responsive to one or more of an age of a user of the intraocular lens system, a sensed distance between the first focal point and the second focal point, a time of day, a sensed intensity of light in the location of the user, a sensed color of light in the location of the user, or any physiological condition of the user.

Figure 11:
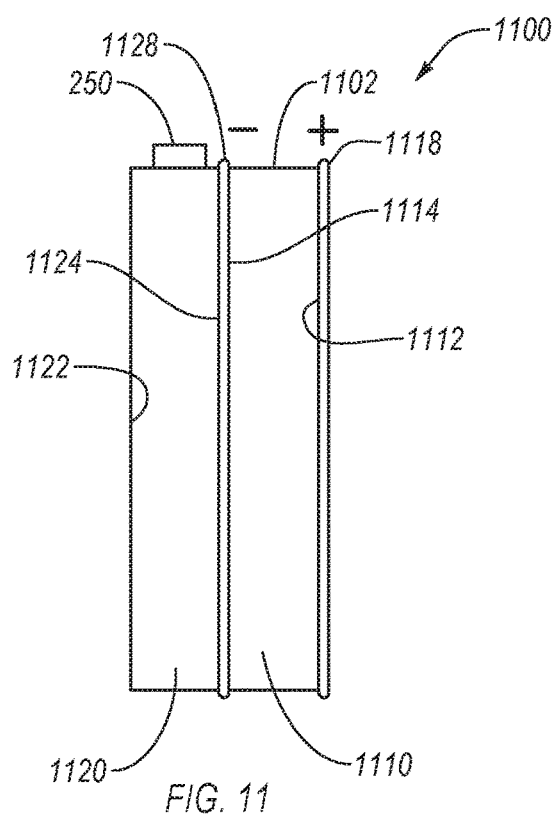
FIGS. 11-12 are side cross-sectional views of portions of diffractive lenses of an IOL system according to various embodiments.

In some embodiments (FIGS. 11, 13A, and 13B), the electrodes can be disposed in different configurations than shown in FIG. 10. For example, at least one of the first and second electrodes can be disposed between the first and second materials. FIG. 11 is a side cross-sectional view of a portions of diffractive lens 1102 of an IOL system 1100 according to an embodiment. The IOL system 1100 includes the diffractive lens 1102 having a first material 1110 and a second material 1120 adjacent thereto. The first and second materials 1110 and 1120 can be similar or identical to any of the first or second materials disclosed herein, in one or more aspects (e.g., material, shape, configuration, presence of diffraction grating, etc.) The first material 1110 can include a first outer surface 1112 and a first interfacial surface 1114 generally opposite thereto. The second material 1120 can include a second outer surface 1122 and a second interfacial surface 1124 generally opposite thereto. One or more of the first interfacial surface 1114 or the second interfacial surface 1124 can include a diffraction grating or pattern therein. One or more of the first material 1110 and the second material 1120 can include an electrically-modifiable index of refraction and, by extension, an electrically-modifiable diffraction pattern (e.g., the physical diffraction pattern may remain the same, while the light refracted therethrough is altered by the change in index of refraction of the material, which causes a change in the effect of the diffraction pattern or diffraction produced therefrom).

As illustrated, the IOL system 1100 can include a first electrode 1118 and a second electrode 1128. The first and second electrodes 1118 and 1128 can be similar or identical to any electrodes disclosed herein, in one or more aspects (e.g., material, leads, etc.). In some embodiments, one of the first electrode 1118 or the second electrode 1128 is disposed between the first material and the second material and the other of the first or second electrodes 1118 or 1128 is adjacent to the first outer surface 1112 of the first material 1110 or the second outer surface 1122 of the second material 1120. For example, the first electrode 1118 can be positioned adjacent to the first material 1110, and the second electrode 1128 can be positioned between the first material 1110 and the second material 1120. The second electrode 1128 can be in direct contact and serve as an interface between the first and second materials 1110 and 1120 such as at the interfacial surfaces 1114 and 1124 thereof. A bias applied to one or both of the first and second electrodes 1118 or 1128 can modify an index of refraction of the first material 1110 and a diffractive pattern therein. In some embodiments, applying a bias to the electrode disposed between the first and second materials 1110 and 1120 can electrically modify the electrically-modifiable index of refraction of both of the first and second materials 1110 and 1120.

The IOL system 1100 can include the controller 250 as described herein. The controller 250 can control the amount of bias applied and the selected duration of time the bias is applied to one or more of the first and second electrodes 1118 or 1128 as disclosed herein. The IOL system 1100 can include one or more sensors as disclosed above.

Figure 12:
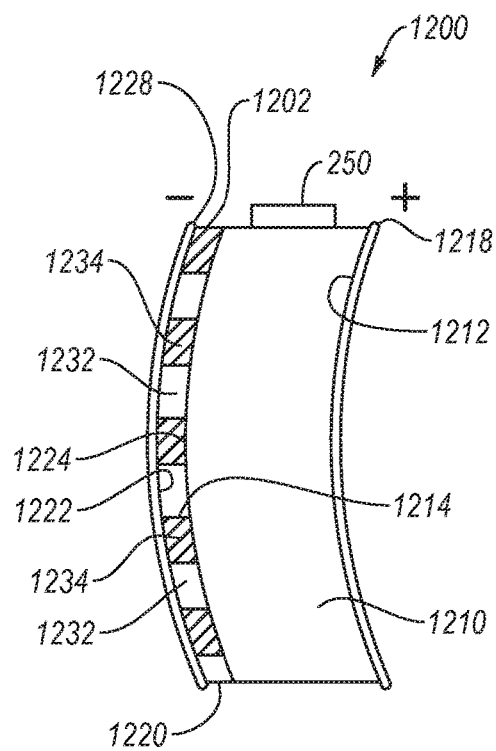

FIG. 12 is a side cross-sectional view of a portions of diffractive lens 1202 of an IOL system 1200 according to an embodiment. The IOL system 1200 includes the diffractive lens 1202, the first and second electrodes 1218 and 1228, and the controller 250. The diffractive lens 1202 can include the first material 1210 and a second material 1220. The first material 1210 and the second material 1220 can be similar or identical to any of the first and second materials disclosed herein, in one or more aspects. For example, the first material can include an outer surface 1212, an interfacial surface 1214 adjacent to (e.g., interfacing) the second material 1220, and a material make-up as disclosed herein. The second material 1220 can include a second outer surface 1222 generally opposite the second interfacial surface 1224. One or more of the first material 1210 and the second material 1220 can have a curved configuration including a curved outer surface (1212 or 1222) or curved interfacial surface (1214 or 1224).

The material make-up of the second material can include a polymer layer 1232 hosting a diffractively patterned electroactive dopant 1234 therein that is positioned and configured to produce a diffraction pattern upon application of an electrical bias thereto. The polymer of the polymer layer 1232 can include any electro-optically inert polymer (e.g., having a substantially fixed index of refraction) suitable for use as a lens or coating thereof such as a polycarbonate (e.g., allyl diglycol carbonate or derivatives thereof), polymethyl methacrylate (PMMA), polypropylene, polyvinyl fluoride (PVDF), polyamide, polyimide, hydrophobic acrylics, hydrophilic acrylics, combinations of the foregoing, or any other plastic or polymeric transparent material suitable for use in an IOL. The electro-active dopant 1234 can include any of the electro-optical (e.g., electrically-modifiable) materials disclosed herein such as lithium niobate, lithium tantalate, lead zirconate titanate, potassium dihydrogen phosphate, cadmium telluride, perovskite lead lanthanum zirconate titanate (PLZT), lead magnesium niobate-lead titanate (PMN-PT) (e.g., $Pb(Mg_{1/3}Nb_{2/3})O_3$—$PbTiO_3$ (PMN-PT)), mixtures of any of the foregoing, or any other suitable substantially transparent material having an electrically-modifiable index of refraction. In some embodiments, the electro-active dopant 1234 can include a liquid crystal polymer.

The electroactive dopant 1234 can be disposed (e.g., patterned) in or on the polymer layer 1232 of the second material 1220 in pattern effective to produce a diffractive grating or pattern and diffraction upon light passing therethrough. The diffractive grating pattern of the electro-active dopant 1234 can be electrically-modifiable to provide or eliminate one or more diffractive orders therein. For example, the diffractive grating pattern can provide a ground state (e.g., no voltage applied thereto) of substantially no diffraction of light passing therethrough, and upon delivery of voltage, the diffraction and pattern thereof is produced, increases, or decreases. In some embodiments, the diffractive grating pattern can provide a ground state diffraction of light passing therethrough, and upon delivery of voltage, the amount of diffraction increases, decreases, or is eliminated. Alternatively or additionally, the first material 1210 can include a polymer layer having a diffractively patterned electroactive dopant therein.

The first electrode 1218 can be disposed adjacent to the first material 1210 (e.g., to the outer surface 1212) and the second electrode 1228 can be disposed adjacent to the second material 1220 (e.g., the outer surface 1222), as described with respect to the electrodes and diffractive lenses disclosed herein. The at least one of the first and second electrodes 1218 or 1228 can extend over at least a portion of the second material 1220 comprising the polymer layer 1232 (including the electro-active dopant 1234 therein). For example, the second electrode 1228 can extend uniformly and continuously over the entire second material 1220 comprising the polymer layer 1232, such as across the entire outer surface 1224. Accordingly, application of voltage to the second electrode 1228 can cause the entirety of the electro-active dopant 1234 in the polymer layer 1232 of the second material 1220 to produce or alter a diffraction pattern in the second material 1220 comprising the polymer layer 1232. Accordingly, in some embodiments, a physical diffraction grating on and between the first and second materials need not be used. While shown without a diffraction pattern at the interfacial surfaces 1214 and 1224, in some embodiments, each of the first interfacial surface 1214 and the second interfacial surface 1224 can include a diffraction surface (e.g., pattern or grating) therein. In some embodiments, the interfacial surfaces 1214 and 1224 can be configured as curved diffraction surfaces substantially as shown in FIG. 6. In such embodiments, one or both of the first and second materials can include an electrically-modifiable index of refraction. The IOL system 1200 can include one or more sensors as disclosed above.

Figure 13A:
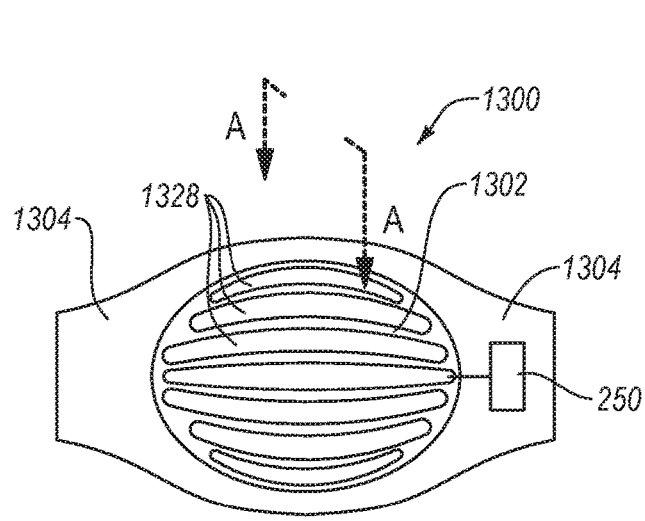
FIG. 13A is a top view of an IOL system according to an embodiment.
Figure 13B:
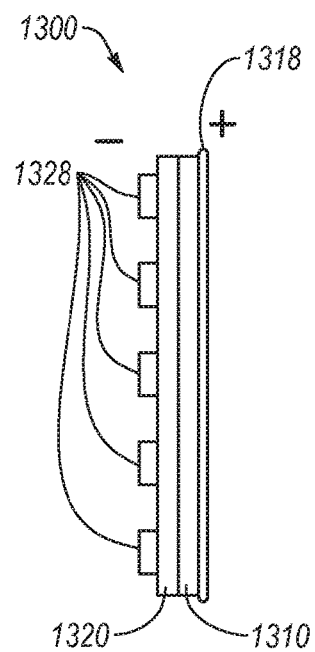
FIG. 13B is a cross-sectional view of a portion of the IOL system of FIG. 13A taken along the plane A-A, according to an embodiment.

In some embodiments, one or more of the electrodes can be positioned and configured to apply bias to only a portion of the electrically-modifiable material(s) in the diffractive lens effective to produce or alter a diffractive pattern therein. FIG. 13A is a top view of an IOL system 1300 and FIG. 13B is a cross-sectional view of a portion of the IOL system 1300 of FIG. 13A taken along the plane A-A, according to an embodiment. The IOL system 1300 can include haptics 1304 and a diffractive lens 1302 including a first material 1310 and a second material 1320, a first electrode 1318, a second electrode 1328, and a controller 250. The first material 1310 the second material 1320, the first electrode 1318, the second electrode 1328, and the controller 250 can be similar or identical to any of the first material(s), a second material(s) 1320, first electrodes, second electrodes, and controllers disclosed herein, in one or more aspects. One or more of the first electrode 1318 and the second electrode 1328 can be spatially patterned effective to apply an electric field sized and spaced to provide a diffractive profile to one or more of the first material 1310 or the second material 1320. For example, at least one of the first electrode 1318 and the second electrode 1328 can be disposed over discrete portions of the first material 1310 and/or the second material 1320 effective to provide a local electrical bias to the electrically-modifiable material in one or more of the first material 1310 and the second material 1320 to provide a diffractive profile or pattern to light passing therethrough. For example and as shown in FIGS. 13A and 13B, the first electrode 1318 can be substantially planar and can cover substantially the entire outer surface of the first material 1310, while the second electrode 1328 can include a plurality of discrete portions (e.g., strips) sized, spaced, and arranged to cause the local portions of second material 1320 adjacent thereto to provide a diffraction pattern or profile to the light passing therethrough. For example, the second electrode 1328 can include a plurality of strips (operably coupled to a power supply) generally arranged substantially in parallel, and sized, and spaced to cause the second material directly in contact therewith (e.g., at the second outer surface 1324) to alter a refractive index upon application of bias to the second electrode 1328, which local refractive indices in the second material can provide a diffractive pattern in the second material. The applied electrical bias of field produced therefrom can be sized and spaced to provide a diffractive profile to the first material effective to change the effective focal length of the diffractive lens from a first effective focal length to a second effective focal length.

In some embodiments, both the first and second electrodes 1318 and 1328 can include the arrangement (e.g., spatial pattern and sizing) disclosed above with respect to the second electrode 1328. The application of the electrical bias to one or more of the first and second electrodes 1318 and 1328 can be carried out via the controller 250 as described herein. In some embodiments, the controller 250 can be disposed in one of the haptics 1304 of the IOL system 1300. In some embodiments, the controller 250 can be disposed at a periphery of the diffractive lens 1302. In some embodiments, the application of bias to the patterned electrode(s) disclosed above can be carried out over any of the durations of time disclosed herein. The IOL system 1300 can include one or more sensors as disclosed above.

Figure 14:
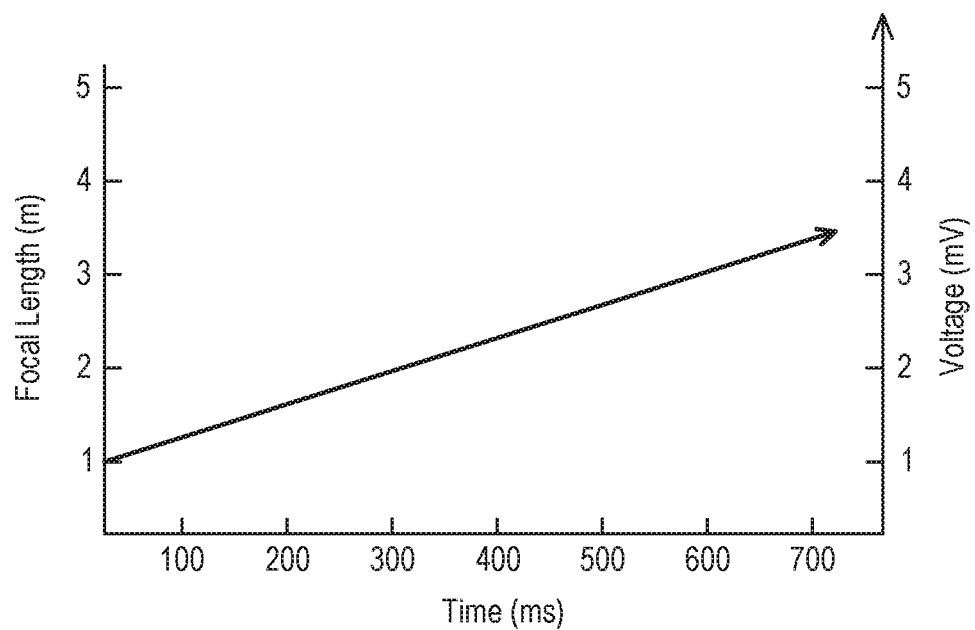
FIG. 14 is a graph of focal length versus time versus voltage according to an embodiment.

FIG. 14 is a graph of focal length versus time versus voltage according to an embodiment. The electrical bias applied to the one or more electrodes in the IOLs disclosed herein can increase or decrease the focal length (e.g., the effective focal length) of the diffractive lens. Such increase or decrease can be time-dependent, based upon the amount of bias applied over a selected duration and the material(s)

in the diffractive lens. For example, the focal length can substantially linearly correspond to the amount of bias (e.g., volts, millivolts, etc.) applied to and by the one or more electrodes over the selected duration. In an embodiment, the at least one controller is configured to substantially linearly increase or decrease the bias to one or more of the first or second electrodes effective to produce a substantially linear transition of a plurality of intermediate focal lengths from the first effective focal length to the second effective focal length. Such a linear increase can be linear over a discrete duration or over any selected duration of time. For example, an increase of 1 millivolt can correspond to an increase in focal length of 1 meter and can be linear over a 300 ms duration of time over which the bias is ramped from the first voltage to the second voltage. This linear relationship can continue throughout the range of increased voltages. In such embodiments, the selected time duration(s) can be reliably used to provide a human perceivably smooth transition between any two focal lengths (as induced by increase/decreases in voltage) by making the selected duration of time larger than the average amount of time that a human eye can accommodate a change in focal lengths. While shown as an increase in focal length, in some embodiments, an increase in voltage can correspond to a decrease in focal lengths; or a decrease in voltage can correspond to an increase in focal length, depending upon the material(s) in the diffractive lens and the diffractive pattern thereof.

The controller can define a characteristic time duration, which is a duration of time required to change the bias from a first bias value associated with the first effective focal length to a second bias value associated with the second effective focal length. The characteristic time duration can be at least about 300 ms, such as about 300 ms to about 2 seconds, about 300 ms to about 400 ms, about 400 ms to about 500 ms, about 500 ms to about 700 ms, about 700 ms to about 1 s, about 300 ms to about 1 s, or less than about 1 s. The characteristic time duration can be dependent upon a capacitance associated with the first and second electrodes. The characteristic time duration can be dependent upon a charge transfer rate associated with the first and second electrodes. The characteristic time duration can be dependent upon the amount of bias applied to the one or more electrodes. The controller can define the characteristic time duration based upon one or more of the preceding criteria.

The controller can select, or a subject can set, the selected duration of time over which the bias is increased from a first bias state to a second bias state (or intermediate bias states as disclosed below). The selected duration of time can be can be at least about 300 ms, such as about 300 ms to about 2 seconds, about 300 ms to about 400 ms, about 400 ms to about 500 ms, about 500 ms to about 700 ms, about 700 ms to about 1 s, about 300 ms to about 1 s, or less than about 1 s. The selected duration of time over which the bias can be transitioned from the first bias state to at least a second bias state can be greater than the characteristic time duration, such as at least 2 times greater, at least 5 times greater, or at least about 10 times greater than the characteristic time duration.

In some embodiments, it can be desirable to transition to a target focal length (e.g., effective focal length) via one or more distinct intermediate focal lengths (e.g., distinct intermediate effective focal lengths), so as to provide small changes in focal length rather than a large jump from one focal length to a relatively distant focal length. Such embodiments can provide a perceivably smoother transition between a first focal length and a target focal length than changing directly between first focal length and the target focal length. In such embodiments, one or more distinct (e.g., discrete) voltages can be utilized to provide one or more distinct (e.g., discrete) intermediate focal lengths between the first focal length and the target focal length.

Figure 15:
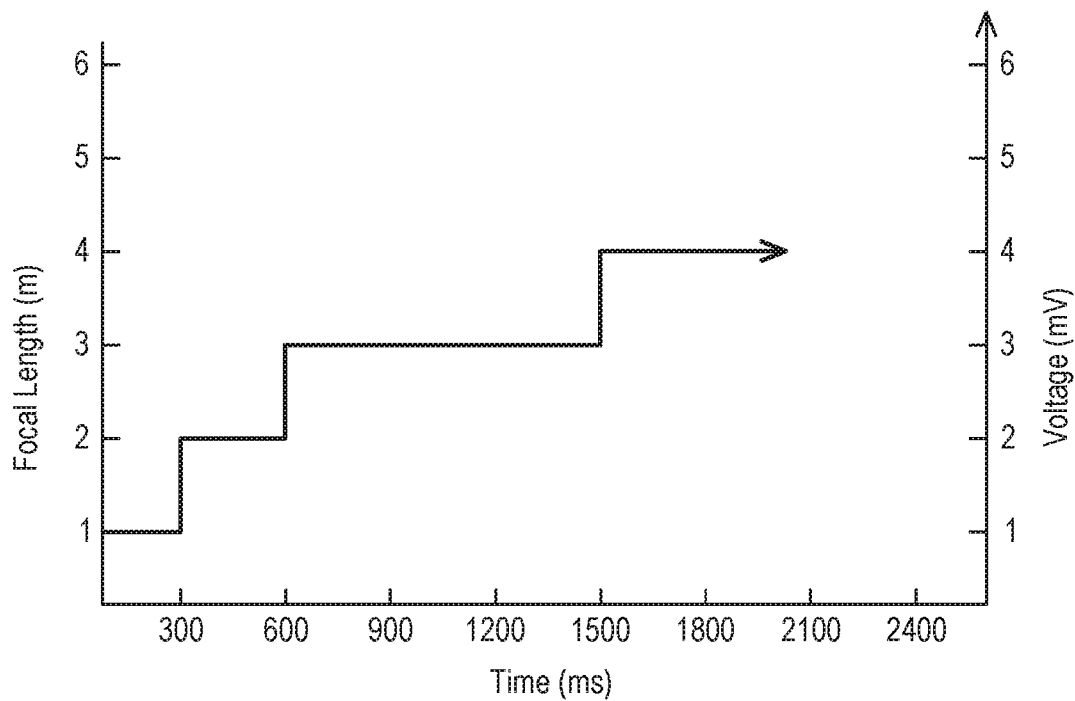
FIG. 15 is a graph of focal length versus time versus voltage according to an embodiment.

FIG. 15 is a graph of focal length versus time versus voltage according to an embodiment. In some embodiments, at least one intermediate bias can be applied to the electrode between a first bias and a target bias (e.g., final bias state). In some embodiments, at least one intermediate bias can include a plurality of distinct intermediate bias states each of which is separated by a distinct amount of bias and each of which includes an incrementally increasing effective focal length approaching the target (e.g., second) effective focal length. In such embodiments, the target or second effective focal length can be shorter or longer than the first effective focal length. In some embodiments, at least one intermediate bias can include a plurality of distinct intermediate bias states each of which is separated by a distinct amount of bias and each of which includes an incrementally decreasing effective focal length approaching the target (e.g., second) effective focal length. In such embodiments, the target or second effective focal length can be shorter or longer than the first effective focal length. The increased or decreased amount of bias can correspond to a desired step (e.g., difference in lengths) between intermediate effective focal lengths, with larger steps being produced by larger differences in intermediate biases. The step(s) or difference between intermediate bias states can be at least about 1 mV, such as about 1 mV to about 1 V, about 5 mV to about 500 mV, about 20 mV to about 300 mV, about 50 mV to about 200 mV, about 1 mV to about 100 mV, about 100 mV to about 300 mV, about 300 mV to about 600 mV, less than 100 mV, or less than 1 V. In an embodiment, the at least one intermediate bias can include an amount of distinct intermediate biases that correspond to equidistant intervals between the first effective focal length and the second effective focal length. In some embodiments, the at least one intermediate bias can include an amount of distinct intermediate biases at least some of which correspond to non-equidistant intervals between the first effective focal length and the second effective focal length.

Upon application of bias, the first effective focal length can immediately change to a second effective focal length. For example, an increase of applied bias from 1 mV to 2 mV can provide a corresponding (a substantially instantaneous) increase in effective focal length of 1 m. In some embodiments, where a change in focal length between 1 m and 4 meters is required, one or more intermediate effective focal lengths may be selected to provide a substantially smooth transition between the 1 m and 12 m focal lengths. Such intermediate effective focal lengths can correspond to intermediate bias states, that is, corresponding intermediate biases, each effective to produce a desired effective intermediate focal length. The intermediate bias states can be selectively applied to produce a corresponding intermediate effective focal length. The intermediate effective focal lengths can exhibit matching or various distances therebetween. For example, each of the one or more intermediate focal lengths can be separated by a substantially identical distance from a successive one of the one or more intermediate focal lengths. The one or more intermediate focal lengths can include a plurality of increasing intermediate focal lengths, each corresponding to an increasing or decreasing amount of bias. The one or more intermediate focal lengths can include a plurality of increasing or decreasing intermediate focal lengths. In some embodiments, the one or more intermediate focal lengths include one intermediate focal length. In some embodiments, the one or more intermediate focal lengths include two or more intermediate (effective) focal lengths, such as about 2 to about 10, about 2 to about 5, about 3 to about 6, about 4 to about 7, less than about 10, or less than about 5 intermediate focal lengths.

The transition from the first bias and focal length to the target bias and focal length can be carried out over a selected duration, with one or more intermediate durations therein. Each of the intermediate durations can correspond to a dwell time at a specific effective focal length. For example, to provide a smooth transition that is not disorienting to the average human eye, it may be desirable to maintain an intermediate effective focal length for a specific amount of time (e.g., longer than the time it takes an eye to accommodate) prior to providing another intermediate or target bias to move the effective focal length at least closer to the target focal length. In such embodiments, the dwell time can be at least about 300 ms, such as about 300 ms to about 2 seconds, about 300 ms to about 400 ms, about 400 ms to about 500 ms, about 500 ms to about 700 ms, about 700 ms to about 1 s, about 300 ms to about 1 s, or less than about 1 s.

In some embodiments having a plurality of distinct intermediate biases and corresponding effective focal lengths, it may be desirable to have substantially equally long dwell times between at least some intermediate effective focal length of the plurality of intermediate effective focal lengths. Such equidistant dwell times can provide a smooth time-dependent transition from the first focal length to the target focal length. In some embodiments having a plurality of distinct intermediate biases and corresponding effective focal lengths, it may be desirable to have different dwell times between at least some of the intermediate effective focal lengths of the plurality of intermediate effective focal lengths, such as to accommodate longer or shorter focal lengths, which may require a longer time to accommodate in the eye. Thus, in some embodiments, it may not be desirable to produce a substantially linear time versus focal length relationship.

The controller can control the time and duration of the bias applied to the electrodes, effective to control the effective focal length of the diffractive lens of the systems disclosed herein. As shown in FIG. 15, the controller can be configured to incrementally increase or decrease the bias to one or more of the first or second electrodes by a distinct amount of bias effective to produce a step-wise transition of one or more intermediate focal lengths from the first effective focal length to the second (e.g., target) effective focal length. In an embodiment, the controller can (or can have machine readable programming stored thereon configured to) selectively adjust a number of the one or more intermediate focal lengths induced by the bias applied to the first and second electrodes, responsive to one or more of an age of a user of the intraocular lens system, a sensed distance between a first focal point and a second focal point, a time of day, a sensed intensity of light in a location of the user, or a sensed color of light in the location of the user.

In some embodiments, a time lag between application of bias and change in focal length can be observed, wherein the application of voltage does not correspond to an immediate change in (effective) focal length of the diffractive lens. Rather, the electro-optical material(s) can have an electrically-modifiable index of refraction that changes (e.g., increases or decreases) at a different rate than a change of the bias that is applied thereto.

Figure 16:
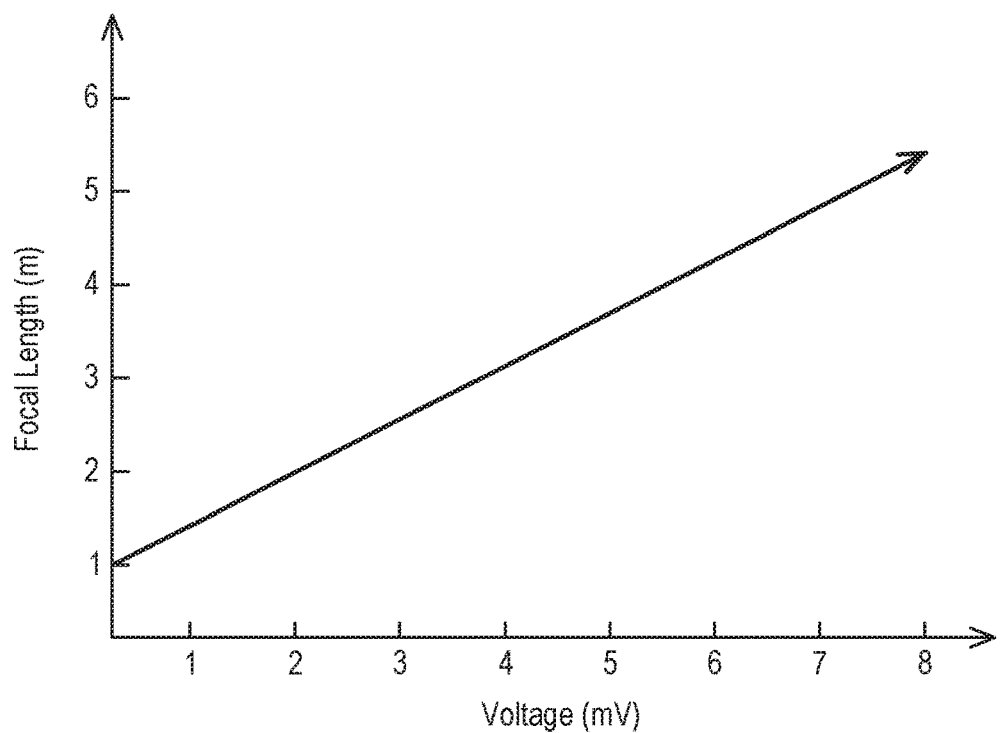
FIG. 16 is a graph of focal length versus voltage according to an embodiment.

FIG. 16 is a graph of focal length versus voltage according to an embodiment. As noted above, the effective focal length can linearly correspond to an applied bias to one or more of the first and second electrodes. Such effective focal length can depend upon one or more of the electrically-modifiable first index of refraction, the first diffraction pattern, the second index of refraction (e.g., an electrically-modifiable second index of refraction), the second diffraction pattern, the first electrode, or the second electrode. Put another way, one or more of the electrically-modifiable first index of refraction, the first diffraction pattern, the second index of refraction, the second diffraction pattern, the first electrode, or the second electrode of the diffractive lens is configured such that a current effective focal length of the diffractive lens substantially linearly corresponds to a current bias applied throughout a range of increasing or decreasing bias. The preceding can be true throughout a range of one or more intermediate bias states. In such embodiments, the controller can specifically select one or more selected durations configured to correspond to an increase or decrease in electrical bias effective to product a desired change in effective focal length of the selected duration of time. Such selective control can be carried out by the processor applying one or more machine readable programs.

In some embodiments, a time lag between application of bias and change in focal length can be observed where the application of voltage does not correspond to an immediate change in (effective) focal length of the diffractive lens. Rather, the electro-optical material(s) can have an electrically-modifiable index of refraction that changes at a slower rate than the bias that is applied thereto.

Figure 17:
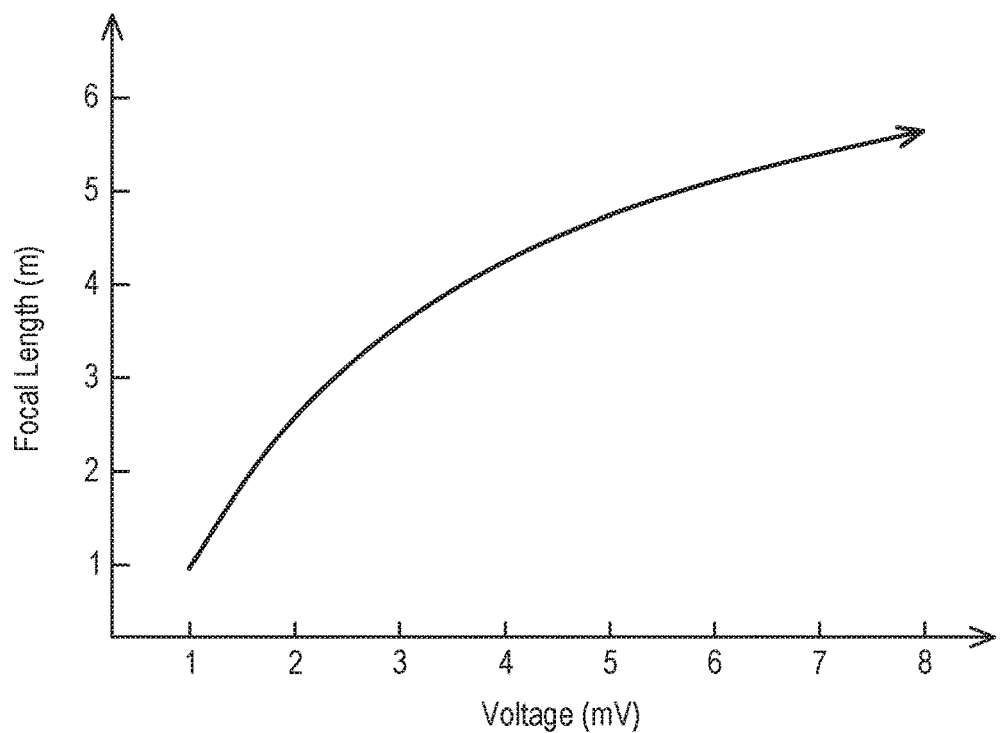
FIG. 17 is a graph of focal length versus voltage according to an embodiment.

FIG. 17 is a graph of focal length versus voltage according to an embodiment. In some embodiments, a mismatch (e.g., lag) between an amount of bias applied to the electrodes and a corresponding effective focal length can be observed over a range of applied biases. For example, one or more of the electrically-modifiable first index of refraction, the first diffraction pattern, the second (e.g., electrically-modifiable) index of refraction, the second diffraction pattern, the first electrode, or the second electrode of the diffractive lens is configured such that a current effective focal length thereof non-linearly corresponds to a current bias applied thereto throughout a range of increasing or decreasing bias. Rather, the electro-optical material(s) can have an electrically-modifiable index of refraction that changes (e.g., increases or decreases) at a different rate than a change of the bias that is applied thereto. Accordingly, a plot of the focal length versus voltage applied to the one or more electrodes can have a curve such as a curve resembling a natural logarithm function or an exponential function curve. Such a natural logarithm function curve as shown in in FIG. 17 can indicate that a material becomes less likely to change an electrically-modifiable index of refraction and associated diffractive property and effective focal length as more bias is applied thereto. Such curves can demonstrate the limits of the materials and ability thereof to change focal length, thereby providing insight into suitable materials for use with certain focal lengths. A medical professional or subject may select one material over another based on limitation of electrical modification and a selected use, such as reading or sightseeing.

Figure 18:
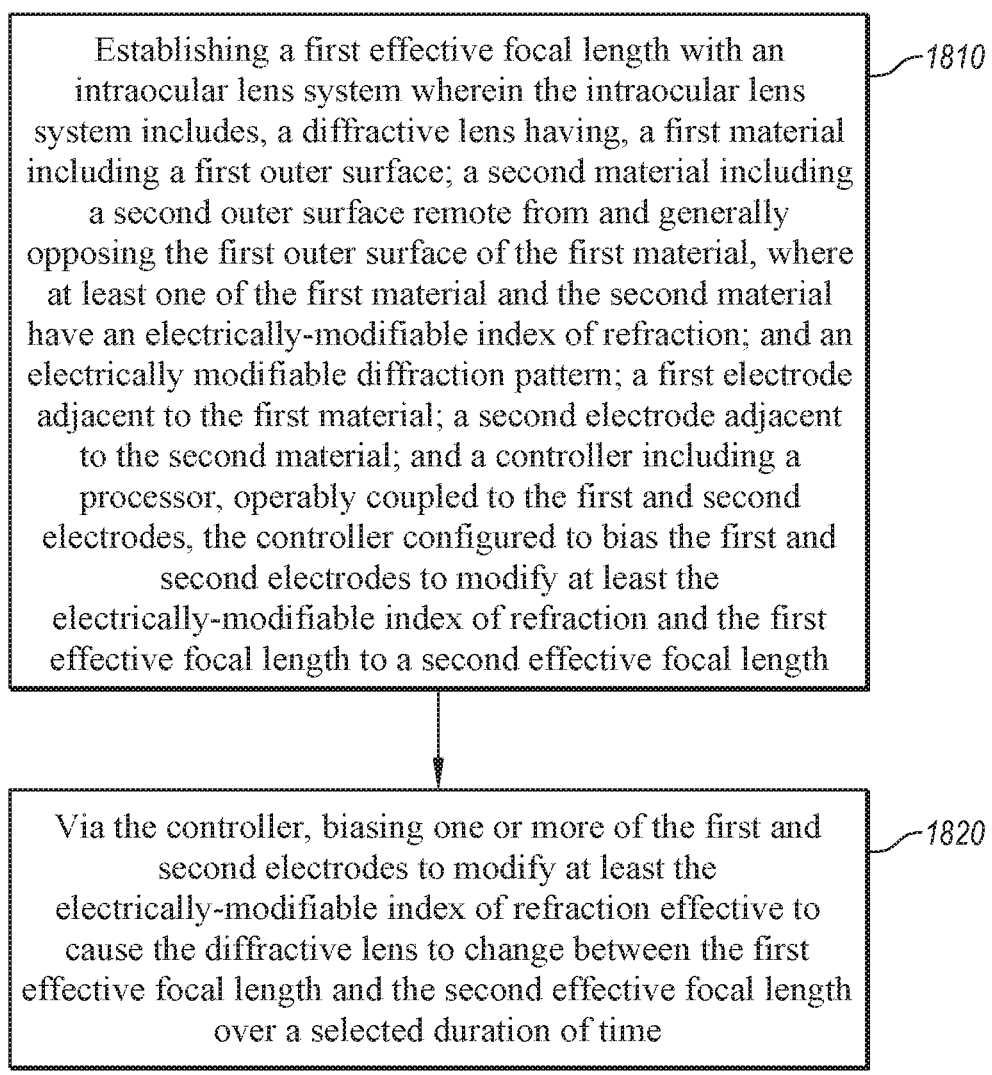
FIG. 18 is a flow chart of a method of selectively modifying a focal length of an IOL system according to an embodiment.

FIG. 18 is a flow chart of a method 1800 of selectively modifying a focal length of an IOL. The method includes an act 1810 of establishing a first effective focal length with an IOL system, wherein the IOL system includes, a diffractive lens having a first material including a first outer surface; and a second material including a second outer surface remote from and generally opposing the first outer surface of the first material, where at least one of the first material and the second material have an electrically-modifiable index of refraction; and an electrically-modifiable diffraction pattern; a first electrode adjacent to the first material; a second electrode adjacent to the second material; and a controller including a processor, operably coupled to the first and second electrodes, the controller configured to bias the first and second electrodes to modify at least the electrically-modifiable index of refraction and a first effective focal length to a second effective focal length; and an act 1820 of via the controller, biasing one or more of the first and second electrodes to modify at least the electrically-modifiable index of refraction effective to cause the diffractive lens to change between the first effective focal length and the second effective focal length over a selected duration of time.

The act 1810 of establishing a first effective focal length with an intraocular lens system can include using any of the IOL systems disclosed herein, or components from any combination of the IOL systems disclosed herein. For example, the IOL system can include a diffractive lens having, a first material including a first outer surface; and a second material including a second outer surface remote from and generally opposing the first outer surface of the first material, where at least one of the first material and the second material have an electrically-modifiable index of refraction; and an electrically-modifiable diffraction pattern. The IOL system can further include a first electrode adjacent to the first material and a second electrode adjacent to the second material. The IOL system can further include a controller including a processor, operably coupled to the first and second electrodes. The controller can include one or more machine readable programs stored in a memory storage medium and a processor configured to carry out the one or more machine readable programs effective to bias the first and second electrodes to modify at least the electrically-modifiable index of refraction and a first effective focal length to a second effective focal length.

Establishing a first effective focal length can include setting a base-line focal length, such as a focal length that is a selected or desirable focal length for most average everyday situations. Establishing a first effective focal length can include setting the first effective focal length in the control as a default focal length. Establishing a first effective focal length can include forming the diffractive lens to provide the first effective focal length in a specific bias state, such as no bias applied thereto. Such formation can include forming the lens from one or more materials each selected to provide an index of refraction and/or curvature effective to cause the diffractive lens to focus light at the first effective focal length when no bias or a first bias is applied thereto. Establishing a first effective focal length can include opening an eye, blinking, or facing an object (e.g., to which a sensor associated with the IOL system designates as the first focal point corresponding to the first focal length).

The act 1820 of biasing one or more of the first and second electrodes can include biasing one or more of the first and second electrodes effective to modify the electrically-modifiable index of refraction of the one or more of the first material or the second material. For example, one or both of the first material and the second material can include an electro-optical material having an electrically-modifiable index of refraction. In such embodiments, biasing the first and second electrodes to modify at least the electrically-modifiable index of refraction can include biasing the first and second electrodes to modify the electrically-modifiable first index of refraction of the first material and the electrically-modifiable second index of refraction of the second material. In some embodiments, biasing the first and second electrodes to modify at least the electrically-modifiable index of refraction can include biasing the first and second electrodes with a substantially identical amount of bias (e.g., voltage) for a substantially identical amount of time. In some embodiments, biasing the first and second electrodes to modify at least the electrically-modifiable index of refraction can include one or more of biasing each of the first and second electrodes at different times or for different amounts of time. In some embodiments, biasing the first and second electrodes to modify at least the electrically-modifiable index of refraction can include biasing each of the first and second electrodes with substantially different amounts of bias (e.g., voltage). In some embodiments, biasing one or more of the first and second electrodes can include biasing one or more of the first and second electrodes with linearly increasing or decreasing voltage over the selected duration of time. Biasing one or more of the first and second electrodes with linearly increasing or decreasing voltage can include causing the first effective focal length of the diffractive lens to substantially linearly increase or decrease to the second effective focal length correspondingly with the linearly increasing or decreasing voltage over the selected duration of time. In some embodiments, the first effective focal length can be greater than the second effective focal length. In some embodiments, the second effective focal length can be greater than the first effective focal length.

In some embodiments, biasing one or more of the first and second electrodes can include biasing one or more of the first and second electrodes with at least one intermediate voltage between a first voltage configured to induce the first effective focal length and a second voltage configured to induce the second effective focal length over the selected duration of time, effective to induce at least one intermediate focal length in the diffractive lens. For example, biasing one or more of the first and second electrodes with at least one intermediate voltage can include biasing one or more of the first and second electrodes with a plurality of distinct intermediate voltages over the selected duration of time, each of which induces a corresponding one of a plurality of intermediate focal lengths. In some embodiments, the plurality of distinct intermediate voltages can include a plurality of increasing or decreasing distinct intermediate voltages, each of which induces a corresponding one of a plurality of increasing or decreasing distinct intermediate focal lengths. In some embodiments, biasing one or more of the first and second electrodes can include increasing or decreasing the bias to the first and second electrodes by one or more distinct amounts effective to produce the one or more distinct intermediate focal lengths between the first effective focal length and the second effective focal length.

In some embodiments, biasing one or more of the first and second electrodes can include selectively adjusting the selected duration of time responsive to one or more of a manufacturer set duration of time, a default duration of time, a last utilized duration of time, an age of a user of the intraocular lens system, a sensed distance between a first focal point and a second focal point, a time of day, a sensed intensity of light in a location of the user, a sensed color of light in the location of the user, or any physiological characteristic of the user (sensed or otherwise). For example, selectively adjusting the selected duration of time can include selectively adjusting the selected duration of time to be less than or greater than the manufacturer set duration of time, the default duration of time, or the last utilized selected duration of time. The manufacturer set duration of time can correspond to an average duration of time that is greater than the time it takes an average human eye of a specific demographic to accommodate between focal points. In some embodiments, selectively adjusting the selected duration of time can include selectively adjusting a duration of one or more intermediate biases effective to adjust a duration of one or more intermediate focal lengths corresponding thereto, within the selected duration of time.

In some embodiments, selectively adjusting the selected duration of time can include automatically adjusting the selected duration of time with the controller responsive to sensor feedback. The methods herein can include using at least one sensor operably coupled to the controller and configured to detect one or more of a distance between a first focal point and a second focal point, a time of day, an intensity of light in a location of a user of the intraocular lens system, or a color of light in the location of the user. For example, one or more sensors can detect an amount of light (e.g., intensity of light) in a location of the user and determine that, based thereon, a longer selected duration of time or shorter selected duration of time may be appropriate, such as a longer selected duration of time in low light or extremely bright light environments. In some embodiments, selectively adjusting the selected duration of time can include automatically adjusting the selected duration of time with the controller responsive to one or more preprogrammed operational parameters, such as a time of day, duration of a gaze, age of the user, an eyeglasses prescription of the user, etc. The methods herein can include sensing one or more of the distance between the first focal point and the second focal point, the time of day, the intensity of light in a location of a user of the IOL system, or the color of light in the location of the user, any physiological characteristic of the user (e.g., subject), or characteristic in the environment of the user. In some embodiments, biasing one or more of the first and second electrodes can include selectively adjusting the selected duration of time responsive to the distance between the first focal point and the second focal point, the time of day, the intensity of light in the location of the user of the intraocular lens system, the color of light in the location of the user, any physiological characteristic of the user (e.g., subject), or characteristic in the environment of the user (e.g., temperature).

In some embodiments, the controller includes a memory storage medium storing one or more machine readable programs, sensor data, user input, or threshold values therein. The controller can include a processor configured to access the memory storage medium and execute machine readable programs, compare sensor data to threshold values, determine selected durations of time, etc. Each of the one or more machine readable programs can include executable instructions for selectively biasing one or more of the first and second electrodes effective to modify the electrically-modifiable index of refraction of one or both of the first and second materials and the effective focal length of the intraocular lens system from the first effective focal length to the second effective focal length over a selected duration of time. In such embodiments, biasing one or more of the first and second electrodes can include activating at least one of the one or more machine readable programs, such as with the processor.

The controller can automatically select the selected duration based on feedback from one or more sensors operably coupled to the controller. The sensors can provide sensor data including any of a sensed distance between a first focal point and a second focal point, a time of day, a sensed intensity of light in a location of the user, a sensed color of light in the location of the user, or any physiological characteristic of the user (sensed or otherwise), such as heart rate, pulse, etc. The controller can compare the sensor data to one or more look-up tables stored therein to determine if the sensor data indicates that a specific selected duration of time should be used. For example, the controller (e.g., processor) can compare the sensor data to a look-up table of threshold values and determine if the sensor data is below, meets, or exceeds a threshold value, and based thereon, automatically provide a selected duration of time or an adjustment thereto. One or more of the adjustment and determination can be carried out (by the processor) according to an operational program stored in the memory storage medium of the controller. The controller can automatically select the duration of time, and direct the application of bias to the one or more electrodes over the duration of time, responsive to the sensor feedback or direction (e.g., user input) via a subject using a user interface operably coupled to the controller. For example, a user can input or select from a number of durations, a specific selected duration of time.

The method 1800 can include programming one or more operational programs, one or more parameters, one or more threshold values, or inputting one or more commands into a user interface operably coupled to the controller 250. For example, selectively adjusting the selected duration of time can include manually adjusting the selected duration of time at the user interface operably coupled to the controller. The user interface can be similar or identical to any user interface disclosed therein. In some embodiments, inputting one or more commands can include inputting or altering the one or more machine readable programs in the memory storage medium, inputting one or more of a selected duration of time, an activation command, a deactivation command, a command to apply a specific amount of bias to one or more of the first or second electrodes, a command to apply a specific amount of bias at a specific rate or specific intervals, or adjustments to any of the foregoing.

In some embodiments, the method 1800 can include defining a characteristic time duration required to change the bias from a first bias value associated with the first effective focal length to a second bias value associated with the with the second effective focal length. Defining the characteristic time duration can include defining the characteristic time duration with the controller. Defining the characteristic time duration can include defining the characteristic time duration as at least partially dependent upon one or more of a capacitance associated with the first and second electrodes, upon a charge transfer rate associated with the first and second electrodes, or an amount of bias applied to one or more of the first and second electrodes. In some embodiments, the controller can define (e.g., select) the selected duration of time as being greater than or less than the characteristic time duration. For example, the controller can define the selected duration of time as at least two times greater than the characteristic time duration, such as about 2 times greater to about 50 times greater, about 2 times greater to about 20 times greater, about 2 times greater to about 10 times greater, about 5 times greater to about 10 times greater, or at least about 10 times greater than the characteristic time duration.

In some embodiments, the method 1800 can include defining a fractional delivery profile of light into each of a set of discrete diffractive orders. Defining a fractional delivery profile of light into each of a set of discrete diffractive orders can include selectively biasing the first and second electrodes to diffract at least a fraction of light into one or more of the set of discrete diffractive orders. Each discrete diffractive order of the set of discrete diffractive orders corresponds to a discrete effective focal length. In some embodiments, the first effective focal length is included in a set of discrete focal lengths defined by a first fractional delivery profile of light into the set of discrete diffractive orders. For example, the first effective focal length can correspond with delivery of a greater amount of light into a first discrete focal length than into any other of the set of discrete focal lengths. The second effective focal length can be included in the set of discrete focal lengths defined by a second fractional delivery profile of light into the set of discrete diffractive orders and the second effective focal length can correspond with delivery of a greater amount of light into a second discrete focal length than into any other of the set of discrete focal lengths. In some embodiments, the method 1800 can include changing the bias applied to one or more of the first electrode or the second electrode effective to change the at least a fraction of light diffracted into one or more of the set of discrete diffractive orders and a corresponding a fraction of light delivered into one or more of the set of discrete focal lengths.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. An intraocular lens system, comprising:
   a diffractive lens configured to be implanted in an eye of a subject, the diffractive lens including,
      a first material having a first outer surface;
      a second material having a second outer surface remote from and generally facing away from the first outer surface, wherein at least the first material includes an electrically-modifiable index of refraction; and
      an electrically-modifiable diffraction pattern defined between the first material and the second material;
   a first electrode on the first outer surface of the first material;
   a second electrode on the second outer surface of the second material; and
   a controller including a processor, operably coupled to the first and second electrodes, the controller configured to selectively bias one or more of the first and second electrodes effective to modify at least the electrically-modifiable index of refraction, the electrically-modifiable diffraction pattern, and an effective focal length of the intraocular lens system from a first effective focal length to a second effective focal length over a selected duration of time that is greater than a duration required for an average human eye to accommodate between the first effective focal length and the second effective focal length.

2. The intraocular lens system of claim 1, wherein each of the first material and the second material have an electrically modifiable index of refraction.

3. The intraocular lens system of claim 1, wherein the controller is configured to selectively bias one or more of the first and second electrodes effective to modify at least the electrically-modifiable index of refraction, the electrically-modifiable diffraction pattern, and the effective focal length of the intraocular lens system from the first effective focal length to the second effective focal length via one or more intermediate focal lengths over a selected duration of time.

4. The intraocular lens system of claim 1, wherein the selected duration of time is up to about 2 seconds.

5. The intraocular lens system of claim 1, wherein the selected duration of time is greater than about 350 milliseconds.

6. The intraocular lens system of claim 1, wherein the controller defines a characteristic time duration required to change the bias from a first bias value associated with the first effective focal length to a second bias value associated with the second effective focal length.

7. The intraocular lens system of claim 6, wherein the characteristic time duration is dependent upon a capacitance associated with the first and second electrodes.

8. The intraocular lens system of claim 6, wherein the characteristic time duration is dependent upon a charge transfer rate associated with the first and second electrodes.

9. The intraocular lens system of claim 6, wherein the selected duration of time is greater than the characteristic time duration.

10. The intraocular lens system of claim 6, wherein the selected duration of time is greater than two times the characteristic time duration.

11. The intraocular lens system of claim 6, wherein the selected duration of time is greater than ten times the characteristic time duration.

12. The intraocular lens system of claim 1, wherein the diffractive lens diffracts light into a set of discrete diffractive orders, and wherein each electrode bias defines a fractional delivery profile of light into each diffractive order of the set of diffractive orders.

13. The intraocular lens system of claim 12, wherein each discrete diffractive order is associated with a discrete focal length.

14. The intraocular lens system of claim 13, wherein the first effective focal length is associated with a set of discrete focal lengths defined by a first fractional delivery profile of light into the set of discrete diffractive orders.

15. The intraocular lens system of claim 14, wherein the first effective focal length is associated with delivery of a greater amount of light into a first discrete focal length than into any other of the set of discrete focal lengths.

16. The intraocular lens system of claim 14, wherein a change in electrode bias is associated with a change in fractional delivery of light into the set of discrete diffractive orders, and a corresponding change in fractional delivery of light into the set of discrete focal lengths.

17. The intraocular lens system of claim 13, wherein the second effective focal length is associated with a set of discrete focal lengths defined by a second fractional delivery profile of light into discrete diffractive orders.

18. The intraocular lens system of claim 17, wherein the second effective focal length is associated with delivery of a greater amount of light into a second discrete focal length than into any other of the set of discrete focal lengths.

19. The intraocular lens system of claim 1, wherein the controller is configured to incrementally increase or decrease the bias to the first and second electrodes by one or more distinct amounts effective to induce one or more distinct intermediate focal lengths between the first effective focal length and the second effective focal length.

20. The intraocular lens system of claim 1, wherein at least one of the first or second electrodes are spatially patterned effective to apply an electric field sized and spaced to provide a diffractive profile to the first material.

21. The intraocular lens system of claim 1, wherein the diffractive lens includes a polymer layer hosting a diffractively patterned electroactive dopant therein that is positioned and configured to produce a diffraction pattern upon application of an electrical field thereto.

22. The intraocular lens system of claim 1, wherein one or more of the electrically-modifiable index of refraction, the electrically-modifiable diffraction pattern, the first electrode, or the second electrode of the diffractive lens is configured such that a current effective focal length thereof substantially linearly corresponds to a current bias applied thereto throughout a range of increasing or decreasing bias.

23. The intraocular lens system of claim 1, wherein one or more of the electrically-modifiable index of refraction, the electrically-modifiable diffraction pattern, the first electrode, or the second electrode of the diffractive lens is configured such that a current effective focal length thereof non-linearly corresponds to a current bias applied thereto throughout a range of increasing or decreasing bias.

24. The intraocular lens system of claim 1, wherein:
the first material includes an electrically-modifiable first index of refraction and a first diffraction surface defining a first diffraction pattern; and
the second material includes a second index of refraction and a second diffraction surface defining a second diffraction pattern, wherein the second diffraction pattern is substantially complementary to the first diffraction pattern.

25. The intraocular lens system of claim 24, wherein:
the controller is configured to apply at least one intermediate bias between a first bias state and a second bias state;
the first bias state corresponds to the first effective focal length and the second bias state corresponds to the second effective focal length; and
the at least one intermediate bias includes an amount of distinct intermediate biases that corresponds to equidistant intervals between the first effective focal length and the second effective focal length.

26. The intraocular lens system of claim 25, wherein one or more of the electrically-modifiable first index of refraction, the first diffraction pattern, the second index of refraction, the second diffraction pattern, the first electrode, or the second electrode of the diffractive lens is configured such that a current effective focal length of the diffractive lens substantially linearly corresponds to a current bias applied throughout a range of increasing or decreasing bias.

27. The intraocular lens system of claim 25, wherein one or more of the electrically-modifiable first index of refraction, the first diffraction pattern, the second index of refraction, the second diffraction pattern, the first electrode, or the second electrode of the diffractive lens is configured such that a current effective focal length thereof non-linearly corresponds to a current bias applied thereto throughout a range of increasing or decreasing bias.

28. The intraocular lens system of claim 1, wherein:
the controller is configured to apply at least one intermediate bias between a first bias state and a second bias state;
the first bias state corresponds to the first effective focal length and the second bias state corresponds to the second effective focal length; and
the at least one intermediate bias corresponds to a least one intermediate focal length between the first effective focal length and the second effective focal length.

29. The intraocular lens system of claim 1, wherein the controller is configured to incrementally increase or decrease the bias to one or more of the first or second electrodes by a distinct amount of bias effective to produce a step-wise transition of one or more intermediate focal lengths from the first effective focal length to the second effective focal length.

30. The intraocular lens system of claim 29, wherein each of the one or more intermediate focal lengths is separated by a substantially identical distance from a successive one of the one or more intermediate focal lengths.

31. The intraocular lens system of claim 29, wherein the one or more intermediate focal lengths include a plurality of increasing intermediate focal lengths each corresponding to an increasing or decreasing amount of bias.

32. The intraocular lens system of claim 29, wherein the one or more intermediate focal lengths include a plurality of decreasing intermediate focal lengths.

33. The intraocular lens system of claim 29, wherein the controller is configured to selectively adjust a number of the one or more intermediate focal lengths induced by the bias applied to the first and second electrodes, responsive to one or more of an age of a user of the intraocular lens system, a sensed distance between a first focal point and a second focal point, a time of day, a sensed intensity of light in a location of the user, or a sensed color of light in the location of the user.

34. The intraocular lens system of claim 1, wherein the controller is configured to selectively adjust the selected duration of time.

35. The intraocular lens system of claim 34, wherein the controller is configured to selectively adjust the selected duration of time responsive to one or more of an age of a user of the intraocular lens system, a sensed distance between a first focal point and a second focal point, a time of day, a sensed intensity of light in a location of the user, or a sensed color of light in the location of the user.

36. The intraocular lens system of claim 1, wherein at least one of the first material or the second material includes an electro-optical material.

37. The intraocular lens system of claim 36, wherein the electro-optical material includes at least one of lithium niobate, lithium tantalate, lead zirconate titanate, potassium dihydrogen phosphate, or cadmium telluride.

38. The intraocular lens system of claim 36, wherein the electro-optical material includes a solid state electro-optical material or includes a liquid crystal.

39. The intraocular lens system of claim 1, wherein:
the second material includes an electro-optical material; and
the controller is configured to selectively bias the first electrode and the second electrode independently, effective to induce one or more intermediate focal lengths between the first effective focal length and the second effective focal length from a collective refraction and diffraction of the first and second materials.

40. The intraocular lens system of claim 39, wherein:
the controller is configured to apply at least one intermediate bias between a first bias state and a second bias state, independently, to each of the first electrode and the second electrode;
the first bias state of each of the first material and the second material corresponds to the first effective focal length and the second bias state of each of the first material and the second material corresponds to the second effective focal length; and
the at least one intermediate bias applied to one or more of the first material and the second material corresponds to the least one intermediate focal length.

41. The intraocular lens system of claim 1, wherein each of the first and second electrodes is substantially transparent to visible wavelength light.

42. The intraocular lens system of claim 1, wherein each of the first and second electrodes includes one or more of indium-tin-oxide, aluminum-doped zinc-oxide, indium-doped cadmium-oxide, or a transparent conductive polymer.

43. The intraocular lens system of claim 1, further comprising at least one sensor operably coupled to the controller and configured to detect one or more of a distance between a first focal point and a second focal point, a time of day, an intensity of light in a location of a user of the intraocular lens system, or a color of light in the location of the user.

44. The intraocular lens system of claim 43, wherein the controller is configured to selectively adjust the selected duration of time responsive to one or more of an age of a user of the intraocular lens system, a sensed distance between the first focal point and the second focal point, a time of day, a sensed intensity of light in the location of the user, or a sensed color of light in the location of the user.

45. The intraocular lens system of claim 43, wherein the controller is configured to selectively adjust a number of one or more intermediate focal lengths induced by the bias applied to the first and second electrodes responsive to one or more of an age of a user of the intraocular lens system, a sensed distance between the first focal point and the second focal point, a time of day, a sensed intensity of light in the location of the user, or a sensed color of light in the location of the user.

46. The intraocular lens system of claim 1, wherein the first electrode is positioned on the first outer surface of the first material and the second electrode is positioned on the second outer surface of the second material.

47. The intraocular lens system of claim 1, wherein the second electrode is in electrical contact with the second outer surface of the second material.

48. An intraocular lens system, comprising:
a diffractive lens configured to be implanted in an eye of a subject, the diffractive lens including,
a first material having a first outer surface;
a second material having a second outer surface remote from and generally facing away from the first outer surface, wherein each of the first material and the second material includes an electrically-modifiable index of refraction; and
an electrically-modifiable diffraction pattern at an interface of the first material and the second material;
a first electrode adjacent to the first material;
a second electrode adjacent to the second material; and
a controller including a processor, operably coupled to the first and second electrodes, the controller configured to selectively bias one or more of the first and second electrodes effective to modify at least the electrically-modifiable index of refraction, the electrically-modifiable diffraction pattern, and an effective focal length of the intraocular lens system from a first effective focal length to a second effective focal length over a selected duration of time.

49. An intraocular lens system, comprising:
a diffractive lens configured to be implanted in an eye of a subject, the diffractive lens including,
a first material having a first outer surface, a first electrically modifiable index of refraction, and a first diffraction surface defining a first diffraction pattern;
a second material having a second outer surface remote from and generally facing away from the first outer surface, a second electrically-modifiable index of refraction, and a second diffraction surface defining a second diffraction pattern that is substantially complementary to the first diffraction pattern;
a first electrode in electrical contact with the first outer surface of the first material;
a second electrode in electrical contact with the second outer surface of the second material; and
a controller including a processor, operably coupled to the first and second electrodes, the controller configured to selectively bias one or more of the first and second electrodes effective to modify at least the first electrically-modifiable index of refraction, the first diffraction pattern, and an effective focal length of the intraocular lens system from a first effective focal length to a second effective focal length over a selected duration of time that is greater than a duration required for an average human eye to accommodate between the first effective focal length and the second effective focal length.

* * * * *